(12) United States Patent
Berry

(10) Patent No.: US 11,291,553 B2
(45) Date of Patent: Apr. 5, 2022

(54) INTERLOCKING SPINAL DISC PROSTHETIC

(71) Applicant: Phoenyx Spinal Technologies, Inc., Tallahasee, FL (US)

(72) Inventor: Bret Michael Berry, Tallahassee, FL (US)

(*) Notice: Subject to any disclaimer, the term of this patent is extended or adjusted under 35 U.S.C. 154(b) by 0 days.

(21) Appl. No.: 16/810,217

(22) Filed: Mar. 5, 2020

(65) Prior Publication Data

US 2021/0275316 A1 Sep. 9, 2021

(51) Int. Cl.
*A61F 2/44* (2006.01)

(52) U.S. Cl.
CPC ........ *A61F 2/442* (2013.01); *A61F 2002/443* (2013.01)

(58) Field of Classification Search
None
See application file for complete search history.

(56) References Cited

U.S. PATENT DOCUMENTS

| | | | |
|---|---|---|---|
| 9,408,714 B1 | 8/2016 | Whipple | |
| 2003/0135277 A1* | 7/2003 | Bryan | A61F 2/4425 623/17.12 |
| 2004/0225363 A1* | 11/2004 | Richelsoph | A61F 2/4425 623/17.13 |
| 2005/0165485 A1 | 7/2005 | Trieu | |
| 2005/0203626 A1* | 9/2005 | Sears | A61F 2/4425 623/17.11 |
| 2005/0209698 A1* | 9/2005 | Gordon | A61B 17/7023 623/17.15 |
| 2007/0010826 A1 | 1/2007 | Rhoda et al. | |
| 2007/0135919 A1* | 6/2007 | Aebi | A61F 2/4425 623/17.11 |
| 2007/0168032 A1 | 7/2007 | Muhanna et al. | |
| 2007/0191958 A1 | 8/2007 | Abdou | |
| 2007/0233251 A1 | 10/2007 | Abdou | |
| 2008/0119933 A1* | 5/2008 | Aebi | A61F 2/4425 623/17.16 |
| 2009/0043391 A1* | 2/2009 | de Villiers | A61F 2/447 623/17.16 |
| 2013/0173005 A1* | 7/2013 | Marnay | A61F 2/30767 623/17.16 |
| 2014/0277469 A1 | 9/2014 | Baynham | |
| 2014/0296985 A1* | 10/2014 | Balasubramanian | A61F 2/44 623/17.16 |

FOREIGN PATENT DOCUMENTS

EP 3597154 A1 1/2020

OTHER PUBLICATIONS

Extended European Search Report for EP Application No. 21160419 dated Aug. 10, 2021.

* cited by examiner

*Primary Examiner* — Tessa M Matthews
(74) *Attorney, Agent, or Firm* — Ellenoff Grossman & Schole LLP; James M. Smedley; Alex Korona

(57) ABSTRACT

The present invention relates generally to a prosthetic spinal disc for replacing a damaged disc between two vertebrae of a spine. The present invention also relates to prosthetic spinal disc designs that have interlocking components.

17 Claims, 23 Drawing Sheets

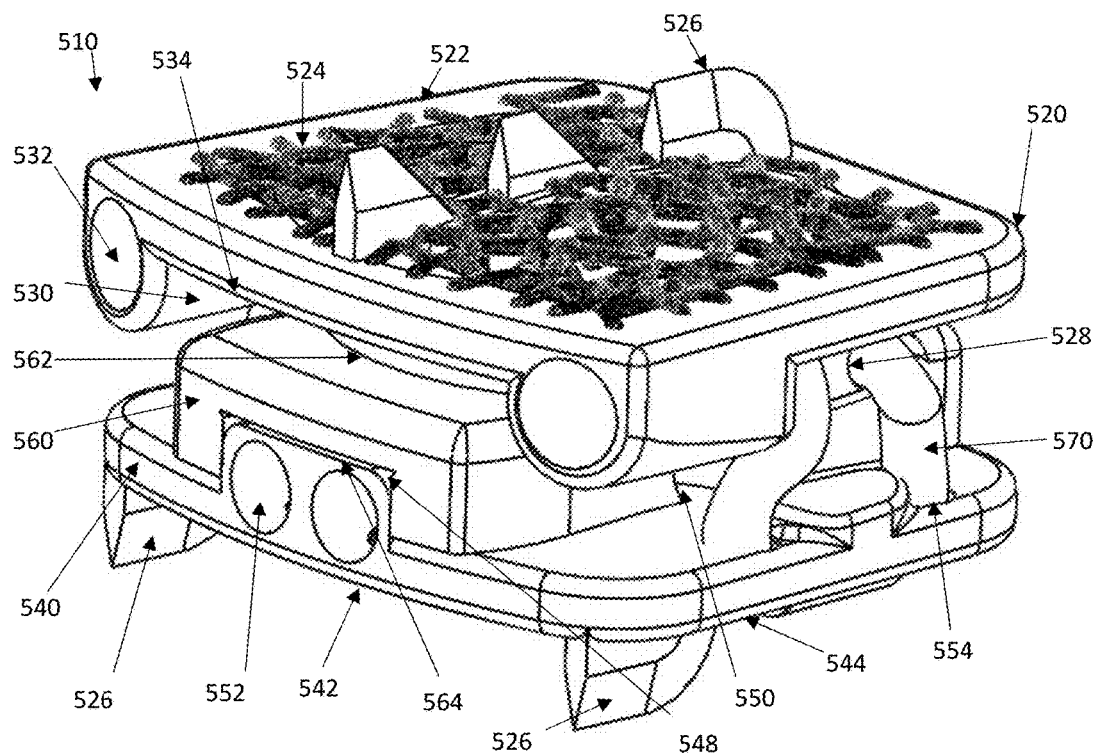
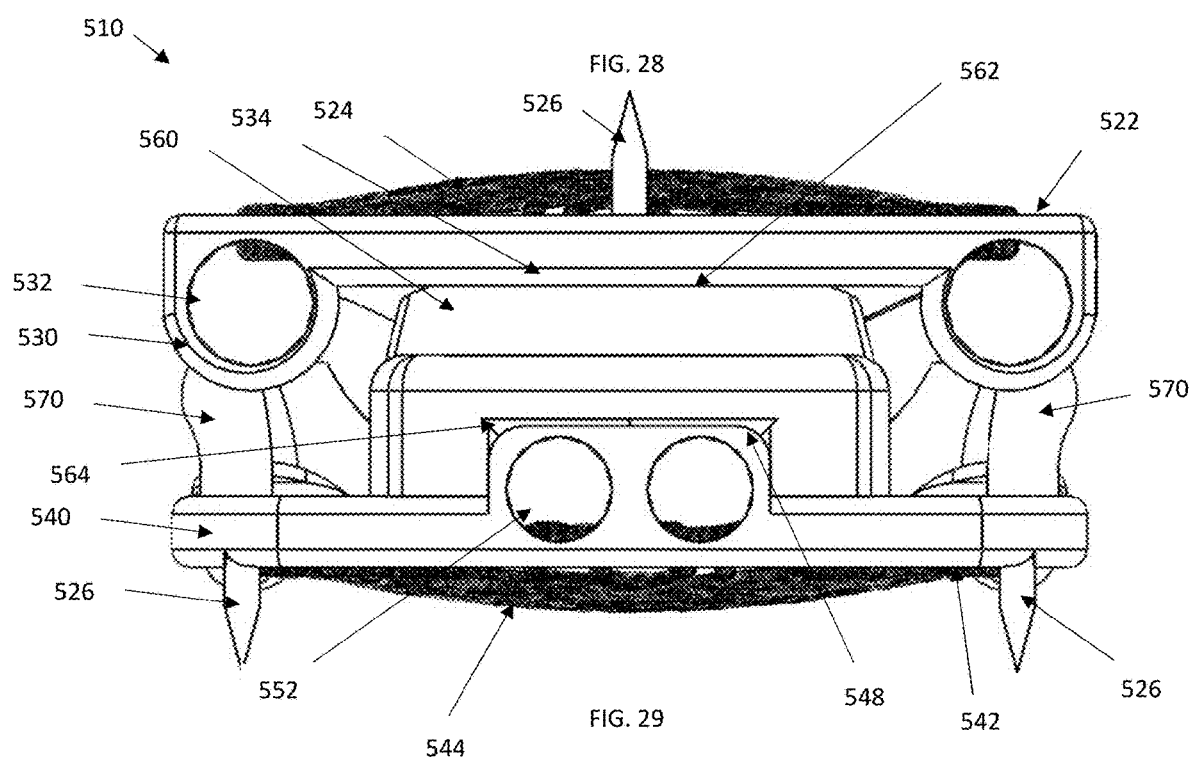

INTERLOCKING SPINAL DISC PROSTHETIC

FIELD OF THE INVENTION

The present invention relates to a prosthetic spinal disc for fully or partially replacing a damaged disc between two vertebrae of a spine. The present invention also relates to prosthetic spinal disc designs that have interlocking components.

BACKGROUND OF THE INVENTION

The vertebrate spine is the axis of the skeleton on which a substantial portion of the weight of the body is supported. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints and allow known degrees of flexion, extension, lateral bending, and axial rotation.

The typical vertebra has a thick anterior bone mass called the vertebral body, with a neural (vertebral) arch that arises from the posterior surface of the vertebral body. The centra of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the posterior side of the spinal cord is known as the lamina. Projecting from the posterior region of the neural 45° arch is the spinous process.

The vertebrae also contains four articular processes that extend from the posterior region of the vertebra. There are two articular processes on the left side of the vertebra and two articular processes on the right side of the vertebra. Two of the four processes (one on the left and one on the right) extend upwards from the top of the laminae and are referred to as the superior articular processes. The other two processes (again one on the left and one on the right) extend downwards from the bottom of the laminae and are referred as the inferior articular processes. In a healthy spine the left and right superior articular processes of a vertebra form synovial joints with the left and right inferior articular processes of the superior adjacent vertebra. These joints are also referred to as facet joints. The facet joints are synovial joints as the joints are encapsulated with connective tissue and lubricated by syn-ovial fluid. The joint faces are also covered with smooth cartilage, which acts to reduce friction and absorb shock.

The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the annulus fibrosus ("annulus") and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc. In other words, a transitional zone is created by the end plates between the malleable disc and the bony vertebrae.

The annulus of the disc is a tough, outer fibrous ring which binds together adjacent vertebrae. The fibrous portion, which is much like a laminated automobile tire, measures about ten to fifteen millimeters in height and about fifteen to twenty millimeters in thickness. The fibers of the annulus consist of fifteen to twenty overlapping multiple plies, and are inserted into the superior and inferior vertebral bodies at roughly a forty degree angle in both directions. This configuration particularly resists torsion, as about half of the angulated fibers will tighten when the vertebrae rotates in either direction, relative to each other. The laminated plies are less firmly attached to each other.

Immersed within the annulus is the nucleus. The healthy nucleus is largely a gel-like substance having high water content, and like air in a tire, serves to keep the annulus tight yet flexible. The nucleus-gel moves slightly within the annulus when force is exerted on the adjacent vertebrae while bending, lifting, and other motions. Additionally, a series of ligaments run along the spine, in effect holding it together. These include anterior longitudinal and lateral longitudinal ligaments.

The spinal disc may be displaced or damaged due to trauma, disease, degenerative defects, or wear over an extended period. A disc herniation occurs when the annulus fibers are weakened or torn and the inner tissue of the nucleus becomes permanently bulged, distended, or extruded out of its normal, internal annulus confines. The mass of a herniated or "slipped" nucleus tissue can compress a spinal nerve, resulting in leg pain, loss of muscle control, or even paralysis. Alternatively, with discal degeneration, the nucleus loses its water binding ability and deflates, similar to the manner in which air is let out of a tire. Subsequently, the height of the nucleus decreases causing the annulus to buckle in areas where the laminated plies are loosely bonded. As these overlapping laminated plies of the annulus begin to buckle and separate, either circumferential or radial annular tears may occur, which may contribute to persistent or disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate back pain from degenerated or herniated discs, the nucleus is removed and the two adjacent vertebrae are surgically fused together. While this treatment alleviates the pain, discal motion is lost in the fused segment. Ultimately, this procedure places a greater stress on the discs adjacent to the fused segment as they compensate for lack of motion, potentially leading to pre-mature degeneration of those adjacent discs.

As an alternative to vertebral fusion, various prosthetic discs have been developed. The first prosthetics embodied a wide variety of ideas, such as ball bearings, springs, metal spikes and other perceived aids. These prosthetics are all made to replace the entire intervertebral disc space and are large and rigid. Many of the current designs for prosthetic discs are large and inflexible and provide minimal articulation. Moreover, few of these prosthetic discs incorporate a stop or resistance to over-extension or rotation. When surgically accessing the disc space, the disc's annulus and the spine's longitudinal ligaments are disrupted and often removed. These anatomical structures prevent over extension of the spine as well as resist rotation. The present invention addresses these issues.

SUMMARY OF INVENTION

The present invention relates generally to a prosthetic spinal disc for replacing a damaged disc between two vertebrae of a spine. In particular, the present invention encompasses a prosthetic spinal disc with interlocking components. These interlocking components allow the implant to resist over extension of the disc space as well as over rotation of the disc space. The components are still able to slide and rotate against one another in order to restore motion to the affected disc space.

In accordance with embodiments of the present invention, an intervertebral prosthetic disc comprises a first endplate having a first surface that engages a first vertebral body and a second surface that is generally u-shaped in the lateral plane. In some examples, the prosthetic disc also has a second endplate having a first surface that engages a second vertebral body and a second surface that is generally u-shaped in the sagittal plane. In some embodiments, the second surface of the endplates interlock each other over an area and may articulate with respect to one another. Additionally, because the u-shaped portions are interlocked, they resist over-rotation of the prosthetic as well as over-extension.

BRIEF DESCRIPTION OF THE DRAWINGS

FIG. 28 is a perspective view of an interlocking prosthetic spinal disc in accordance with a sixth embodiment of the present invention.

FIG. 29 is an anterior view of an interlocking prosthetic spinal disc in accordance with a sixth embodiment of the present invention.

DETAILED DESCRIPTION OF ILLUSTRATIVE EMBODIMENTS

In the Summary above and in this Detailed Description, and the claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

In accordance with embodiments of the present invention, the interlocking prosthetic spinal disc disclosed herein is configured to be implanted into a spine, to imitate the functions of a healthy spinal disc, for example, by providing and permitting the same mobility and load carrying ability of a healthy spinal disc.

Figure 1:
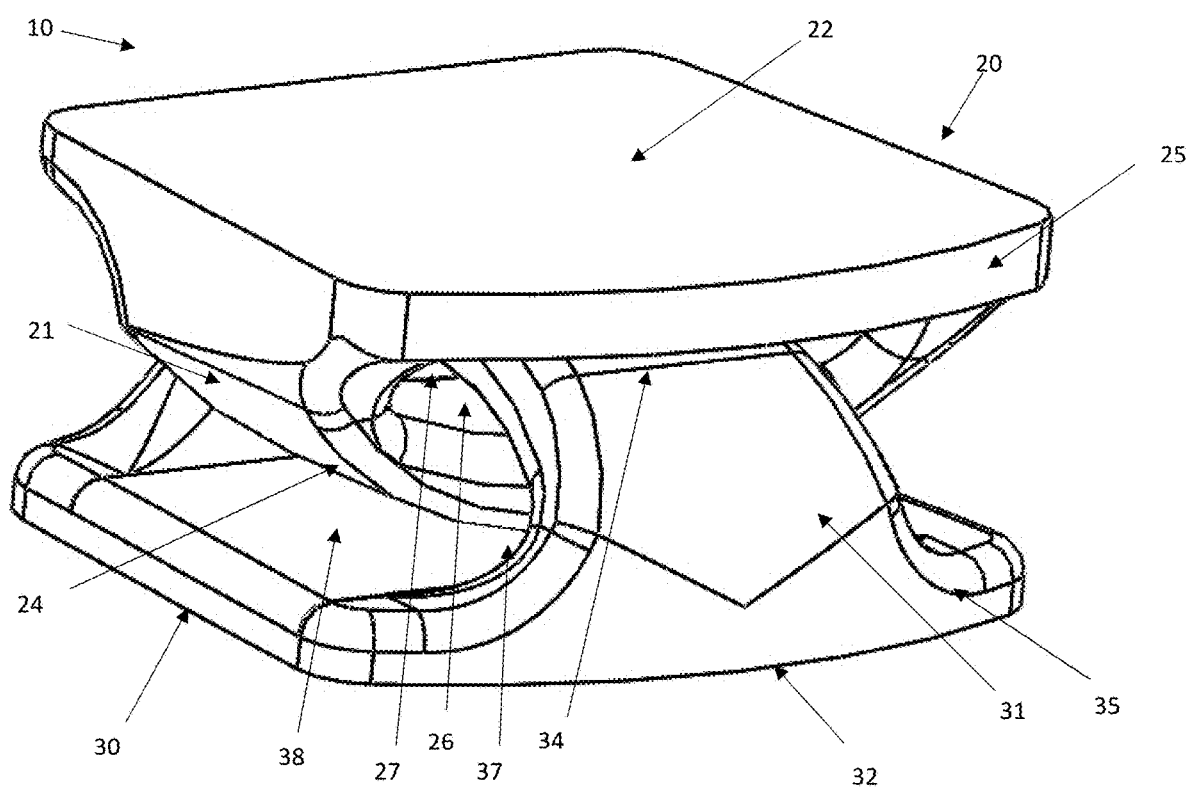
FIG. 1 is a perspective view of an interlocking prosthetic spinal disc in accordance with a first embodiment of the present invention.

First Exemplary Embodiment:

FIG. 1 depicts a perspective view of an interlocking prosthetic spinal disc in accordance with an embodiment of the present invention. In FIG. 1, the interlocking prosthetic spinal disc 10 comprises a first endplate component 20 and a second endplate component 30. In the illustrated example, the first endplate component 20 is comprised of a first base 25 and a first u-shaped element 21. In the depicted example, the second endplate component 30 includes a second base 35 and a second u-shaped element 31. In some embodiments, the u-shaped elements 21 and 31 are formed of a resilient material. In some embodiments, the u-shaped elements 21 and 31 are flexible. In the illustrated example, an exterior portion of the first endplate component 20 includes a vertebral mating surface 22. In the depicted example, an exterior portion of the second endplate component 30 includes a vertebral mating surface 32. The first base 25 and the second base 35 are contemplated to have the orientation of any geometric shape, including: squares, rectangles, circles, ovals, pentagons, hexagons, triangles. One of ordinary skill in the art would appreciate that there are numerous suitable and advantageous arrangements for the geometric orientation of the first and second bases depending on the specific intended use application of the particular interlocking prosthetic spinal disc and embodiments of the present invention are contemplated for use with any such prosthetic spinal disc arrangements.

Figure 2:
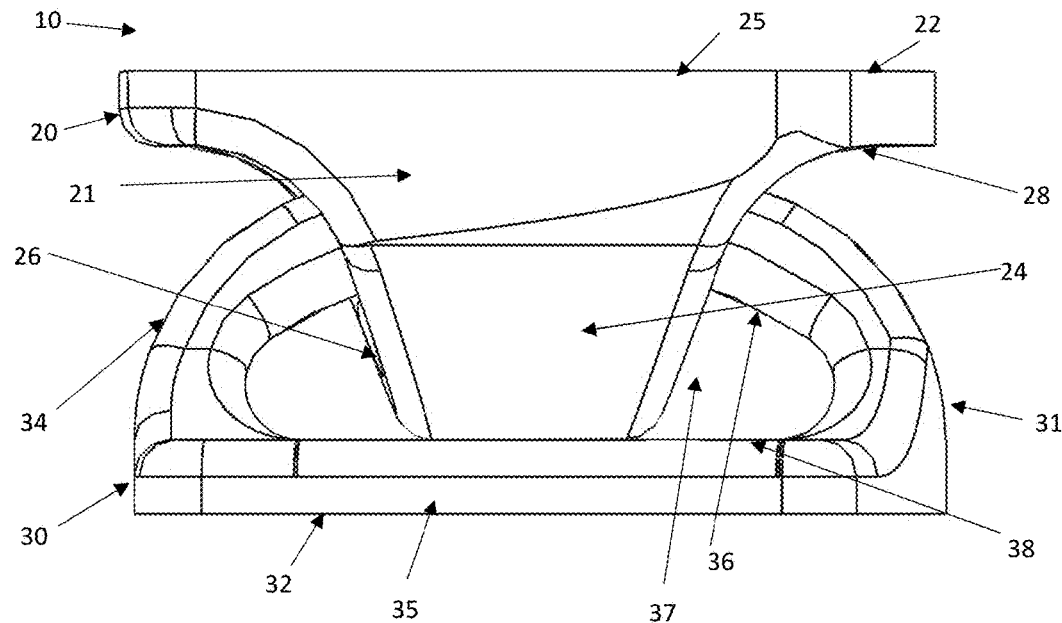
FIG. 2 is lateral view of an interlocking prosthetic spinal disc in accordance with a first embodiment of the present invention.

FIG. 2 depicts a lateral view of an interlocking prosthetic spinal disc in accordance with an embodiment of the present invention. In the depicted example, the first endplate component 20 includes a first base 25 having a base articulation surface 28 on an interior surface thereof and a vertebral mating surface 22 on an exterior surface thereof. In some embodiments, the base articulation surface 28 is flat. In some embodiments, the base articulation surface 28 is concave. In an illustrative example, the base articulation surface 28 permits the articulation or movement of the second u-shaped element 31 against the first base 25. In the illustrated example, a u-shaped element 21 comprising an exterior articulating surface 24 and an interior articulating surface 26 extends from the first base 25. In some embodiments, the u-shaped element extends from the base articulation surface 28. In the depicted example, the exterior articulating surface 24 is generally convex. In the illustrated example, the interior articulating surface 26 is generally concave. In the depicted example, the u-shaped element 21 of the first endplate component 20 extends from one side of the base 25 to a second side of the base 25. In the depicted example, disposed between the u-shaped element 21 and the base 25 is an aperture 27 configured to receive a second u-shaped element 31. In the illustrated example, the second endplate component 30 includes a second base 35 having a base articulation surface 38 on an interior surface thereof and vertebral mating surface 32 on an exterior surface thereof. In some embodiments, the base articulation surface 38 is flat. In some embodiments, the base articulation surface 38 is concave. In the illustrated example, the second u-shaped element 31 comprising an exterior articulating surface 34 and an interior articulating surface 36 extends from the second base 35. In some embodiments, the u-shaped element 31 extends from the base articulation surface 38. In the depicted example, the exterior articulating surface 34 is generally convex. In the illustrated example, the interior articulating surface 36 is generally concave. In the depicted example, the u-shaped element 31 of the second endplate component 30 extends from one side of the base 35 to a second side of the base 35. In the depicted example, disposed between the u-shaped element 31 and the second base 35 is an aperture 37 configured to receive the u-shaped element 21. In the illustrated example, a portion of the first u-shaped element 21 is received within the aperture 37 of the u-shaped element 31 and a portion of the u-shaped element 31 is received within the aperture 27 of the u-shaped element 21, interlocking the first u-shaped element 21 with the second u-shaped element 31.

Figure 3:
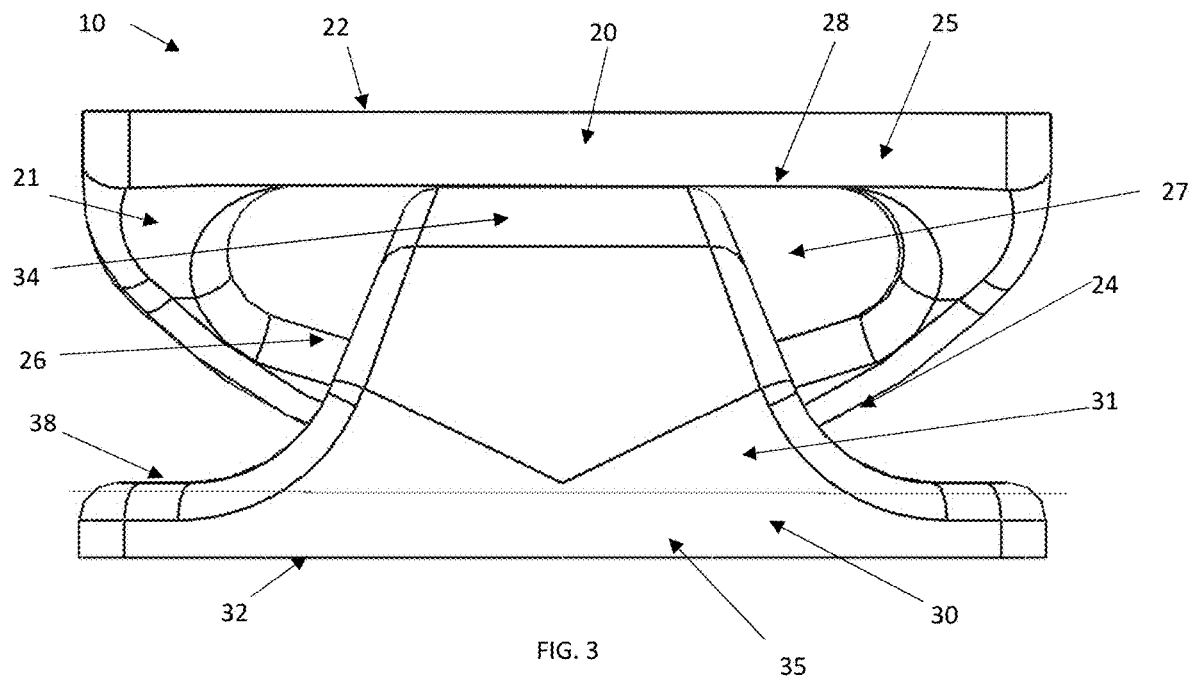
FIG. 3 is an anterior view of an interlocking prosthetic spinal disc in accordance with a first embodiment of the present invention.

FIG. 3 depicts an anterior view of an interlocking prosthetic spinal disc in accordance with an embodiment of the present invention. In the depicted example, the interior surface of the first endplate component 20 includes the base articulation surface 28. In the illustrated example, the u-shaped element 21 extends from the base articulation surface 28. In the depicted example, the interior surface of the second endplate component 30 includes the base articulation surface 38. In the illustrated example, the u-shaped element 31 extends from the base articulation surface 38. As shown in the depicted example, the first u-shaped element 21 is interlocked with the second u-shaped element 31. In the depicted example, the exterior articulating surface 24 of the first u-shaped element 21 rests on the base articulation surface 38 of the second endplate component 30. In the illustrated example, the exterior articulating surface 24 of the first u-shaped element 21 is configured to articulate on the base articulation surface 38 of the second endplate component 30. Similarly, in the depicted example, the base articulation surface 28 of the first endplate component 20 is rests on the exterior articulating surface 34 of the second u-shaped element 31. Moreover, in the illustrated example, the exterior articulating surface 34 of the second endplate component 30 is configured to articulate on the base articulation surface 28 of the first endplate component 20.

In any embodiment, the u-shaped elements 21 and 31 may be substantially round. In some embodiments, the u-shaped elements 21 and 31 may have substantially oval profiles. In some embodiments, the u-shaped elements may include edges. In some embodiments, the u-shaped elements may be substantially square. One of ordinary skill in the art would appreciate that there are numerous suitable and advantageous arrangements for the u-shaped elements depending on the specific intended use application of the particular interlocking prosthetic spinal disc and embodiments of the present invention are contemplated for use with any such prosthetic spinal disc arrangements.

Figure 4:
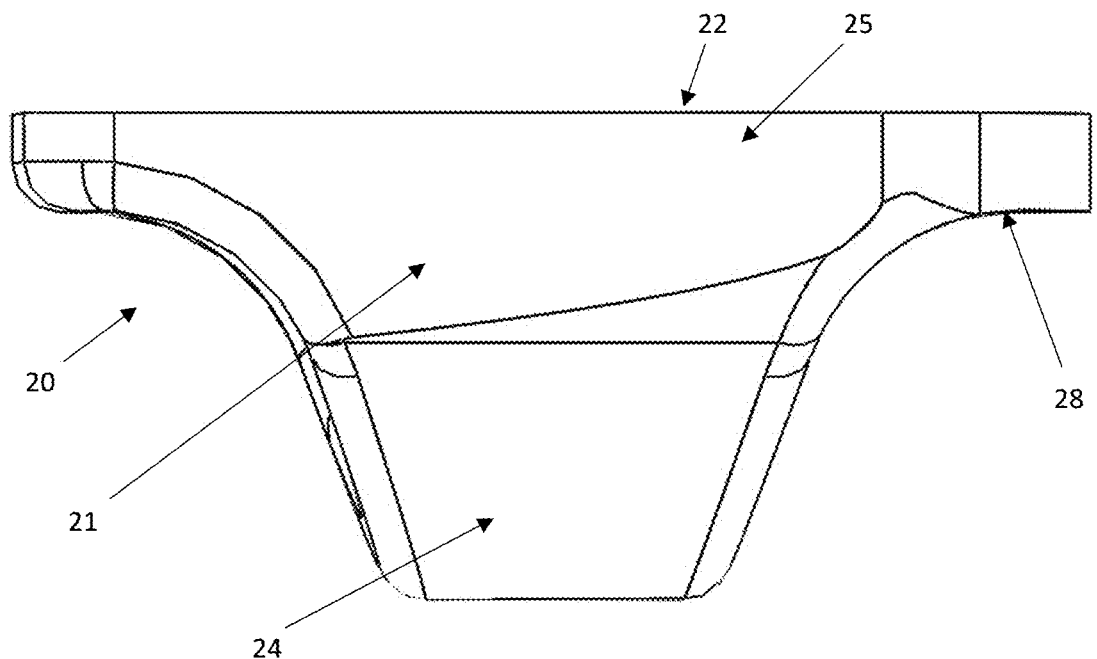
FIG. 4 is a lateral view of a first endplate component of an interlocking prosthetic spinal disc in accordance with a first embodiment of the present invention.
Figure 5:
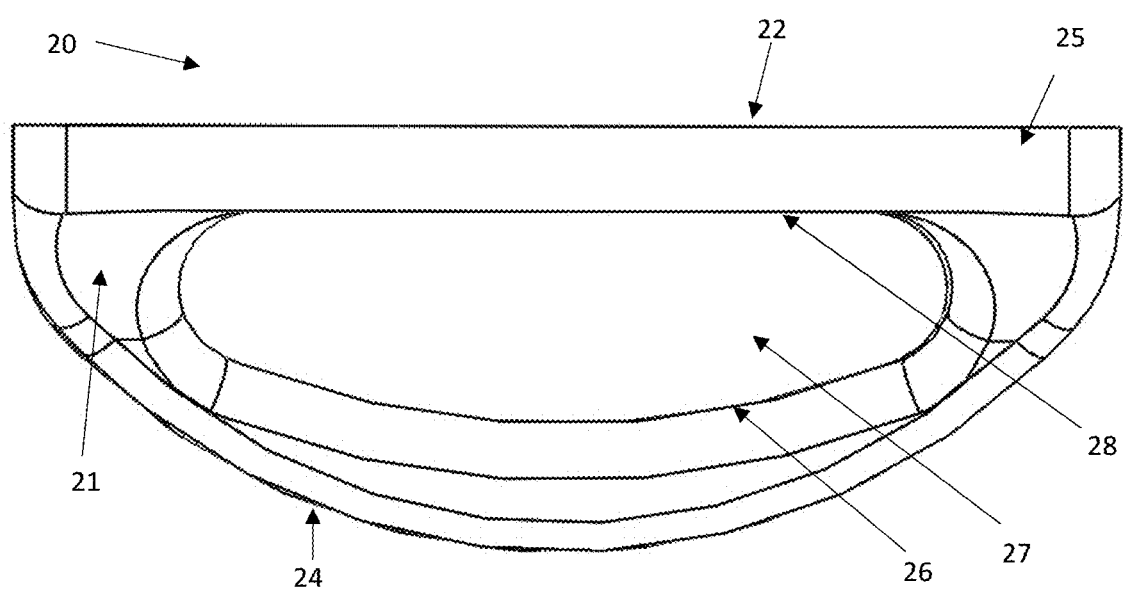
FIG. 5 is an anterior view of a first endplate component of an interlocking prosthetic spinal disc in accordance with a first embodiment of the present invention.

FIGS. 4 and 5 depict lateral and anterior views of a first endplate component of an interlocking prosthetic spinal disc in accordance with a first embodiment of the present invention. In the depicted example, the first endplate component 20 includes a vertebral mating surface 22 on a top side, opposing a base articulation surface 28 on a bottom side. In the illustrated embodiment, the u-shaped element 21 extends from the interior surface of the first base 25. In the depicted embodiment, the u-shaped element 21 connects with the interior surface of the first base 25 at least at two points. In the illustrated example, an aperture 27 disposed between the first base 25 and the first u-shaped element 21 is configured to receive the second u-shaped element 31.

Figure 6:
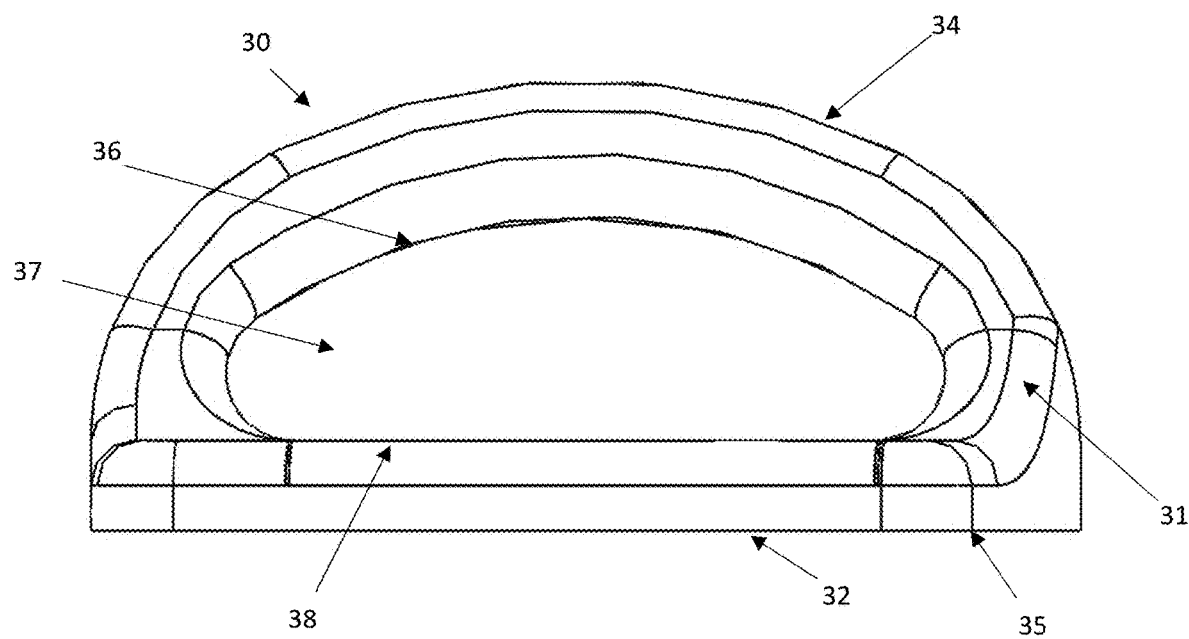
FIG. 6 is a lateral view of a second endplate component of an interlocking prosthetic spinal disc in accordance with a first embodiment of the present invention
Figure 7:
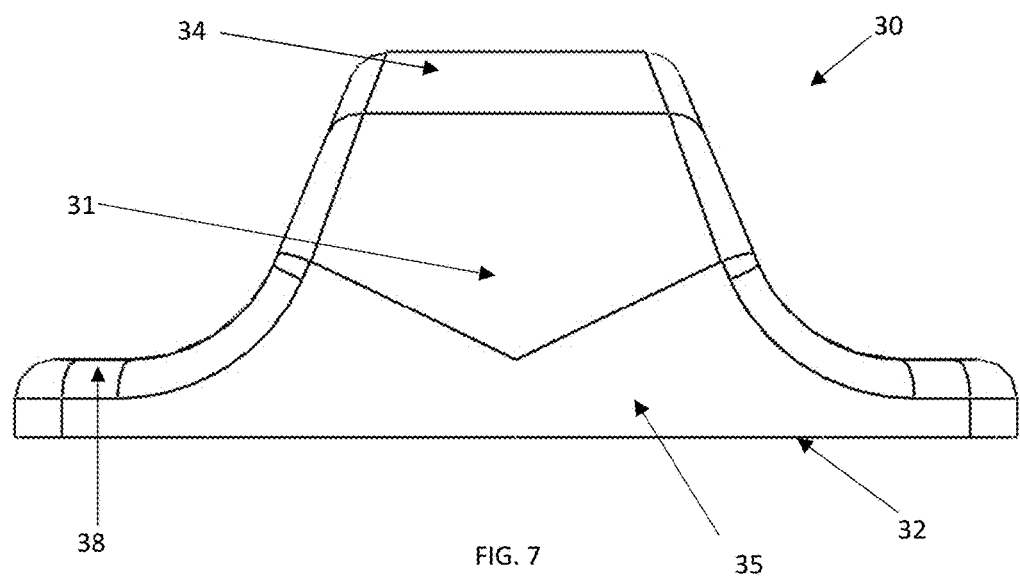
FIG. 7 is an anterior view of a second endplate component of an interlocking prosthetic spinal disc in accordance with a first embodiment of the present invention.

FIGS. 6 and 7 depict lateral and anterior views of a second endplate component of an interlocking prosthetic spinal disc in accordance with a first embodiment of the present invention. In the depicted example, the second endplate component 30 includes a vertebral mating surface 32 on a top side, opposing a base articulation surface 38 on a bottom side. In the illustrated embodiment, the u-shaped element 31 extends from the interior surface of the second base 35. In the depicted embodiment, the u-shaped element 31 connects with the interior surface of the second base 36 at least at two points. In the illustrated example, an aperture 37 disposed between the second base 35 and the second u-shaped element 31 is configured to receive the first u-shaped element 21.

Figure 8:
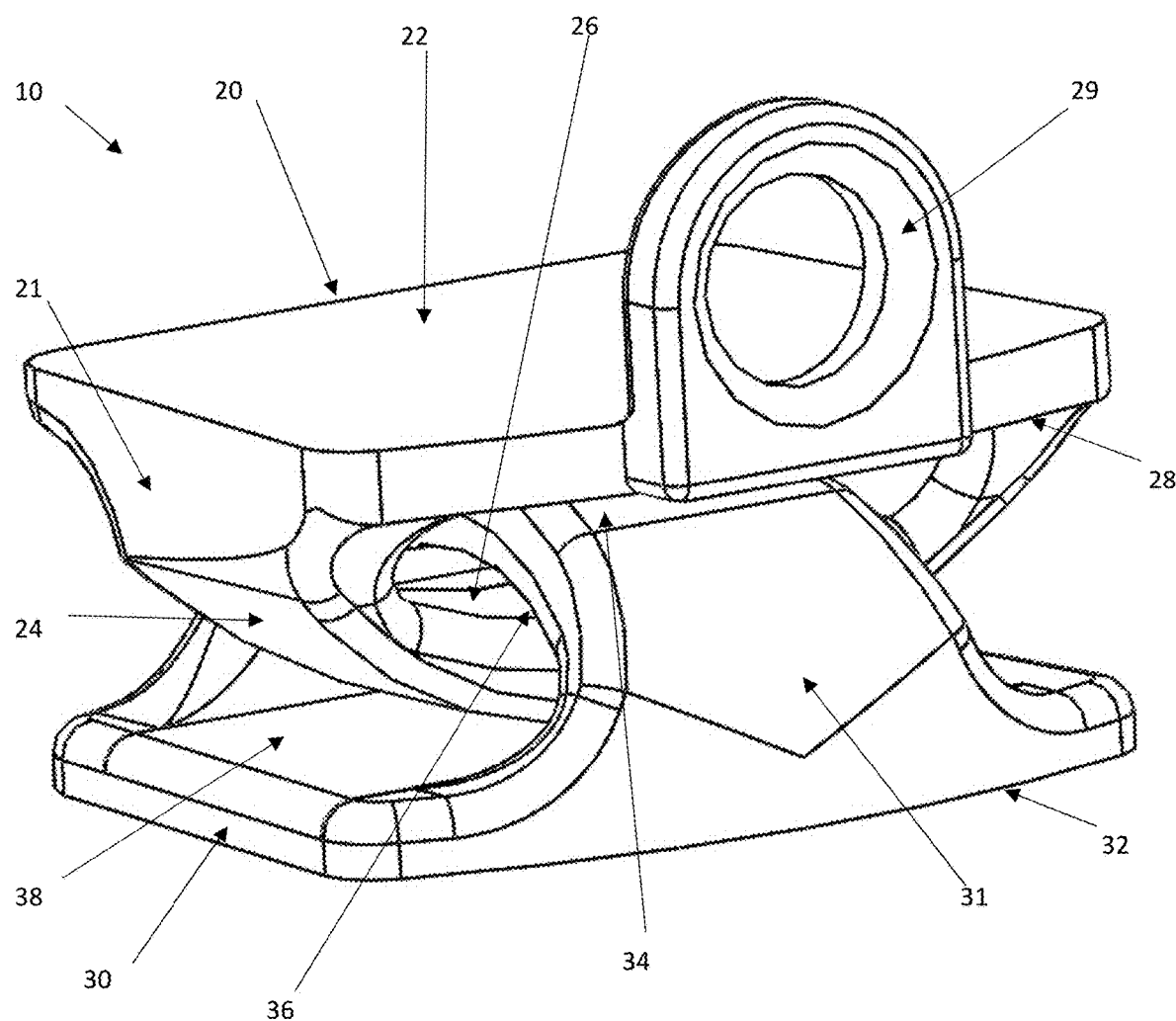
FIG. 8 is a perspective view of an interlocking prosthetic spinal disc with a fastening aperture in accordance with a first embodiment of the present invention.

FIG. 8 depicts a perspective view of an interlocking prosthetic spinal disc with a fastening aperture in accordance with a first embodiment of the present invention. In the depicted example, the interlocking prosthetic spinal disc 10 is comprised of a first endplate component 20 and a second endplate component 30. In the depicted example, the first endplate component 20 includes a first base 25 having a base articulation surface 28 on an interior surface thereof and a vertebral mating surface 22 on an exterior surface thereof. In the illustrated example, a u-shaped element 21 comprising an exterior articulating surface 24 and an interior articulating surface 26 extends from the interior surface of the first base 25. In the depicted example, the exterior articulating surface 24 is generally convex. In the illustrated example, the interior articulating surface 26 is generally concave. In the depicted example, the u-shaped element 21 of the first endplate component 20 extends from one side of the first base 25 to a second side of the base 25. In the illustrated example, the second endplate component 30 includes a second base 35 having a base articulation surface 38 on an interior surface thereof and vertebral mating surface 32 on an exterior surface thereof. In any embodiment, the vertebral mating surfaces 22 and 32 may include spikes, teeth or porous areas to connect with vertebral bodies. In the depicted example, a u-shaped element 31 comprising an exterior articulating surface 34 and an interior articulating surface 36 extends from the interior surface of the second base 35. In the depicted example, the exterior articulating surface 34 is generally convex. In the illustrated example, the interior articulating surface 36 is generally concave. In the depicted example, the u-shaped element 31 of the second endplate component 20 extends from one side of the second base 35 to a second side of the base 35. In the illustrated example, the first endplate component 20 includes a fastening aperture 29. In the depicted example, the fastening aperture 29 extends from the first base 25. In some embodiments, the second base includes a fastening aperture 29. In some embodiments, either or both of the first base 25 and the second base 35 include one or more fastening apertures 29. In some embodiments, the fastening aperture 29 is configured to receive a fastener (not shown). In any embodiment, the fastener may be a screw, pin or similar fastening member. In accordance with various embodiments, the fastener (not shown) is inserted through the fastening aperture 29 to engage with a vertebral body, thereby securing the first endplate component 20 to the vertebral body.

Figure 9:
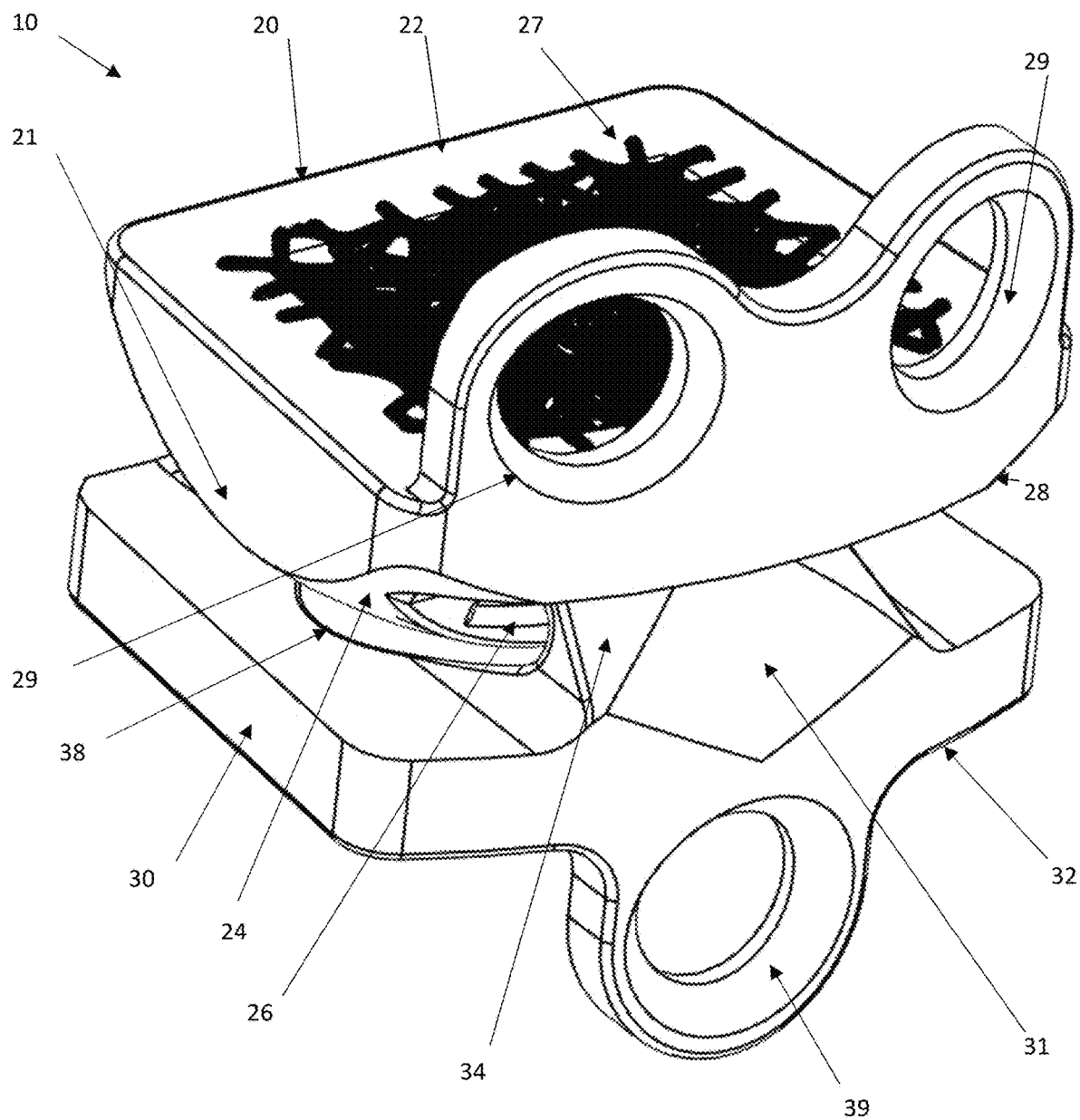
FIG. 9 depicts a perspective view of an interlocking prosthetic spinal disc configured with a porous bony ingrowth region and a plurality of fastening apertures in accordance with a first embodiment of the present invention.

FIG. 9 depicts a perspective view of an interlocking prosthetic spinal disc configured with a porous bony ingrowth region and fastening apertures in accordance with a first embodiment of the present invention. In the depicted example, the interlocking prosthetic spinal disc 10 is comprised of a first endplate component 20 and a second endplate component 30. In the depicted example, the first endplate component 20 includes a first base 25 having a base articulation surface 28 on an interior surface thereof and a vertebral mating surface 22 on an exterior surface thereof. In the illustrated example, a porous bone ingrowth surface 50 is located on the vertebral mating surface 22. In any embodiment, the porous bone ingrowth surface 50 is configured to promote bony ingrowth. In some embodiments, the porous bone ingrowth surface 50 is an osteoconductive material. In some embodiments, the porous bone ingrowth surface 50 may have a porous or macrotexture surface to promote bone growth. In the illustrated example, a u-shaped element 21 comprising an exterior articulating surface 24 and an interior articulating surface 26 extends from the first base 25. In the depicted example, the exterior articulating surface 24 is generally convex. In the illustrated example, the interior articulating surface 26 is generally concave. In the depicted example, the u-shaped element 21 of the first endplate component 20 extends from one side of the first base to a second side of the first base 25. In the illustrated example, the second endplate component 30 includes a second base 35 having a base articulation surface 38 on an interior surface thereof and vertebral mating surface 32 on an exterior surface thereof. In the depicted example, a u-shaped element 31 comprising an exterior articulating surface 34 and an interior articulating surface 36 extends from the second base 35. In the depicted example, the exterior articulating surface 34 is generally convex. In the illustrated example, the interior articulating surface 36 is generally concave. In the depicted example, the u-shaped element 31 of the second endplate component 20 extends from one side of the second base 35 to a second side of the second base 35. In the illustrated example, the first endplate component 20 and the second endplate component 30 include fastening apertures 29. In any embodiment, one or more fastening apertures may be disposed on either or both of the first and second endplate components 20 and 30. The fastening apertures 29 are configured to receive and engage with a fastener (not shown) in order to secure the prosthetic disc 10 to bone. In accordance with various embodiments, the fastener (not shown) is inserted through the aperture 39 to engage with a vertebral body, thereby securing the second endplate component 30 to the vertebral body.

In any embodiment, the interlocking prosthetic spinal disc 10 may be 3D printed with the first endplate component 20 being printed concurrently with the second endplate component 30. Various embodiment implementations may include the u-shaped element 21 of the first endplate component 20 and the u-shaped element 31 of the second endplate component 30 printed to be interlocking with one another.

In an example illustrative of the design and operation of various embodiment implementations, the interior articulating surface 26 of the first u-shaped element 21 is configured to link with the interior articulating surface 36 of the second u-shaped element 31. In an illustrative example, the interior articulating surface 26 of the first u-shaped element 21 is configured to articulate against the interior articulating surface 36 of the second u-shaped element 31. In various embodiments, the u-shaped element 21 of the first endplate component 20 and the u-shaped element 31 of the second endplate component 30 interlock with one another, preventing the two components from separating.

In another example illustrative of the design and operation of various embodiment implementations, the interlocked u-shaped elements 21 and 31 prevent over extension of the vertebral joint once the prosthetic spinal disc 10 is implanted. Moreover, the opposing orientation of the u-shaped element 21 and the u-shaped element 31 prevents over-rotation of each of the first and second endplate components 20 and 30, respectively. In an illustrative example, the second u-shaped element 31 and the first u-shaped element 21 are configured to rest against and limit the movement of one another as the prosthetic spinal disc 10 rotates with the joint.

Figure 10:
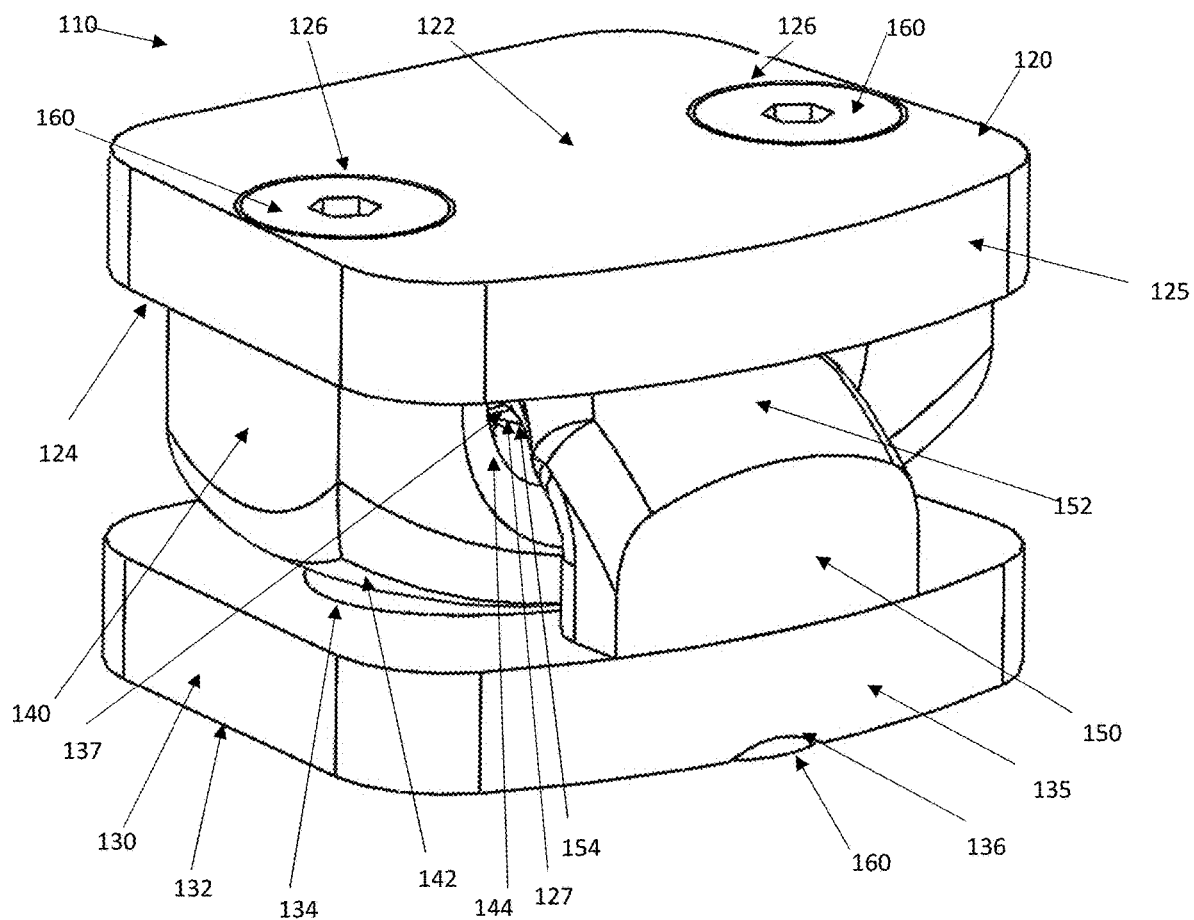
FIG. 10 is a perspective view of an interlocking prosthetic spinal disc in accordance with a second embodiment of the present invention.

Second Exemplary Embodiment:

FIG. 10 is a perspective view of a prosthetic spinal disc in accordance with a second embodiment of the present invention. In the depicted example, the prosthetic spinal disc 110 is comprised of a first endplate component 120 and a second endplate component 130. In the illustrated example, a first u-shaped element 140 is connected to an interior portion of the first endplate component 120. Specifically, in the depicted example, the first u-shaped element 120 is connected an interior surface of a first base 125 of the first endplate component 120. Similarly, in the illustrated example, a second u-shaped element 150 is connected to the second endplate component 130. Specifically, in the depicted example, the second u-shaped element 150 is connected to an interior portion of a second base 135 of the second endplate component 130. In the depicted example, a first aperture 127 is disposed between the first u-shaped element 140 and the first base 125. In the illustrated example, the first aperture 127 is configured to receive and hold the second u-shaped element 150. Likewise, in the depicted example, a second aperture 137 is disposed between the second u-shaped element 150 and the second base 135. In the illustrated example, the second aperture 137 is configured to receive and hold the first u-shaped element 140. In the illustrated example, the first u-shaped element 140 is configured to articulate within the second aperture 137 and the second u-shaped element 150 is configured to articulate within the first aperture 127. In the depicted example, the first endplate component 120 includes a vertebral mating surface 22 on a top side, opposing a base articulation surface 124 on a bottom side. In some embodiments, the base articulation surface 124 is flat. In some embodiments, the base articulation surface 124 is concave. In some embodiments, either or both of the first base 125 and the second base 135 include one or more fastening holes 126 for receiving fasteners 160 configured to secure the first u-shaped element 140 to the first base 125 and the second u-shaped element 150 to the second base 135. In any embodiment, the fasteners 160 may be screws, pins, or any similar fastening members. In the depicted example, the first u-shaped element 140 is fastened to the first base 125 by two fasteners 160.

Figure 11:
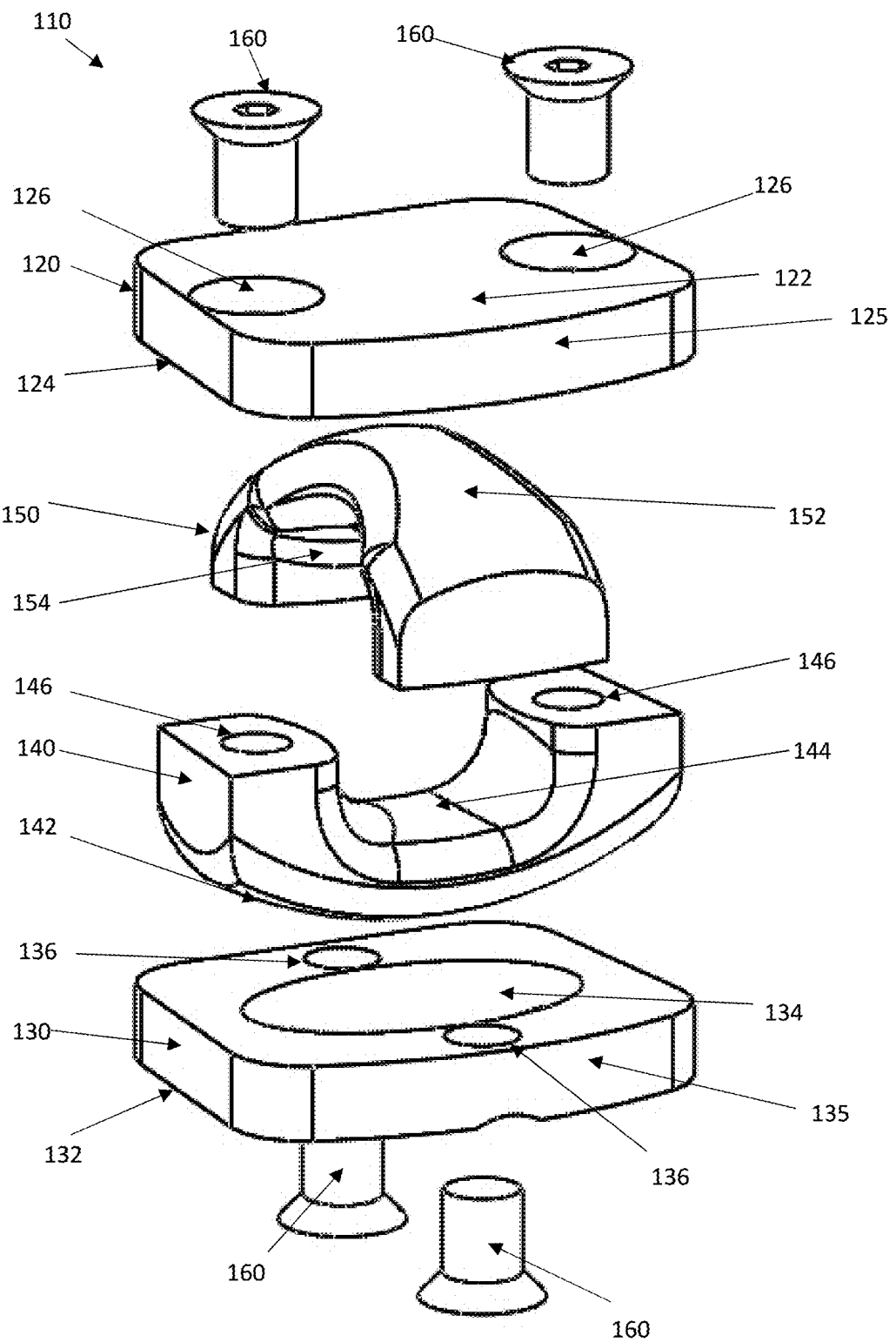
FIG. 11 is an exploded view of an interlocking prosthetic spinal disc in accordance with a second embodiment of the present invention.

FIG. 11 is an exploded view of an interlocking prosthetic spinal disc in accordance with a second embodiment of the present invention. In the depicted example, the first u-shaped element 140 and the second u-shaped element 150 are fastened to the first base 125 and the second base 135, respectively, by fasteners 160. In some embodiments, the first base 125 and the second base 135 may each include one or more fastening holes 136 for receiving fasteners 160 configured to secure the u-shaped elements to the bases. In some embodiments, the u-shaped elements 140 and 150 include one or more holes 146 configured to receive the fasteners 160 and fasten the u-shaped elements 140 and 150 to the first base 125 and the second base 135, respectively. In the illustrated example, the fasteners 160 extend through the fastening holes 126 and 136 and into holes 146 disposed on the first u-shaped element 140 and the second u-shaped element 150, respectively. In some embodiments the holes 146 are threaded, corresponding to the threads of the fasteners 160. In accordance with various embodiments, the first u-shaped element 140 is configured to articulate against and interlock with the second u-shaped element 150.

In an example illustrative of the design and operation of various embodiment implementations, to assemble the interlocking prosthetic spinal disc 110, the two u-shaped elements 140 and 150 are configured to correspond with one another. In various embodiments, the two u-shaped elements 140 and 150 are fastened to the first base 125 and the second base 135, respectfully, with fasteners 160. In some embodiments, the interior articulating surface 144 of the first u-shaped element 140 is configured to connect with the interior articulating surface 154 of the second u-shaped element 150. In an illustrative example, the interior articulating surface 144 of the first u-shaped element 140 is configured to articulate against the interior articulating surface 154 of the second u-shaped element 150. In various embodiments, the first u-shaped element 140 and the second u-shaped element 150 interlock with one another, preventing the two components from separating. In any embodiment, the width of the u-shaped elements 140 and 150 may define the bounds of articulation of the first and second endplate components 120 and 130.

In another example illustrative of the design and operation of various embodiment implementations, the interlocked u-shaped elements 140 and 150 prevent over extension of the vertebral joint once the prosthetic spinal disc 110 is implanted. Moreover, the opposing orientation of the u-shaped element 140 and the u-shaped element 150 prevents over-rotation of each of the first and second endplate components 120 and 130, respectively. In an illustrative example, the second u-shaped element 150 and the first u-shaped element 140 are configured to rest against and limit the movement one another as the prosthetic spinal disc 110 moves or rotates with the joint.

Figure 12:
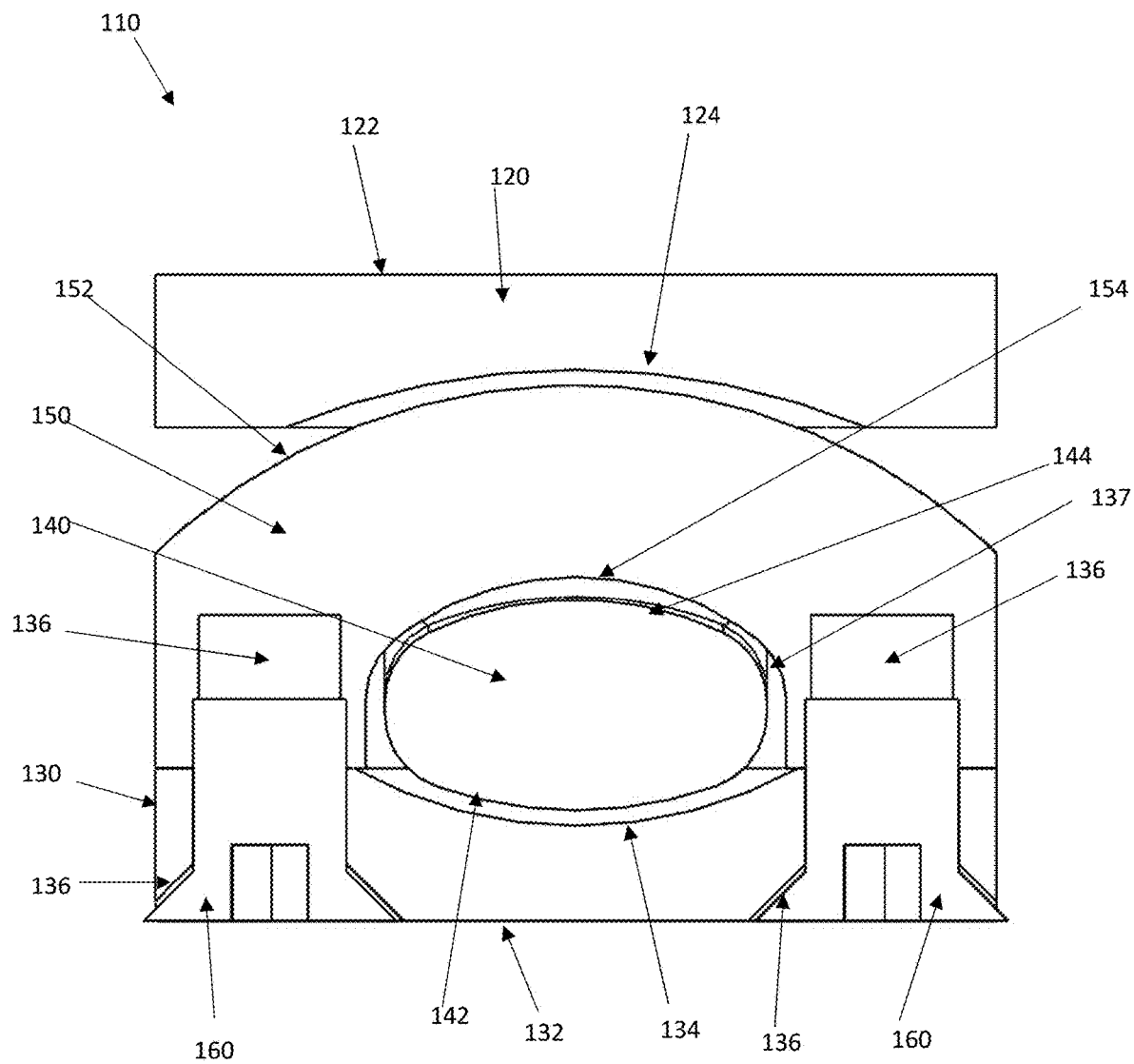
FIG. 12 is a lateral cross sectional view of an interlocking prosthetic spinal disc in accordance with a second embodiment of the present invention.

FIG. 12 is a lateral cross sectional view of an interlocking prosthetic spinal disc in accordance with a second embodiment of the present invention. In the depicted embodiment, an aperture 127 is disposed between the first u-shaped element 140 and the interior surface of the first base 125. In the depicted example, the aperture 127 is configured to receive the second u-shaped element 150.

Figure 13:
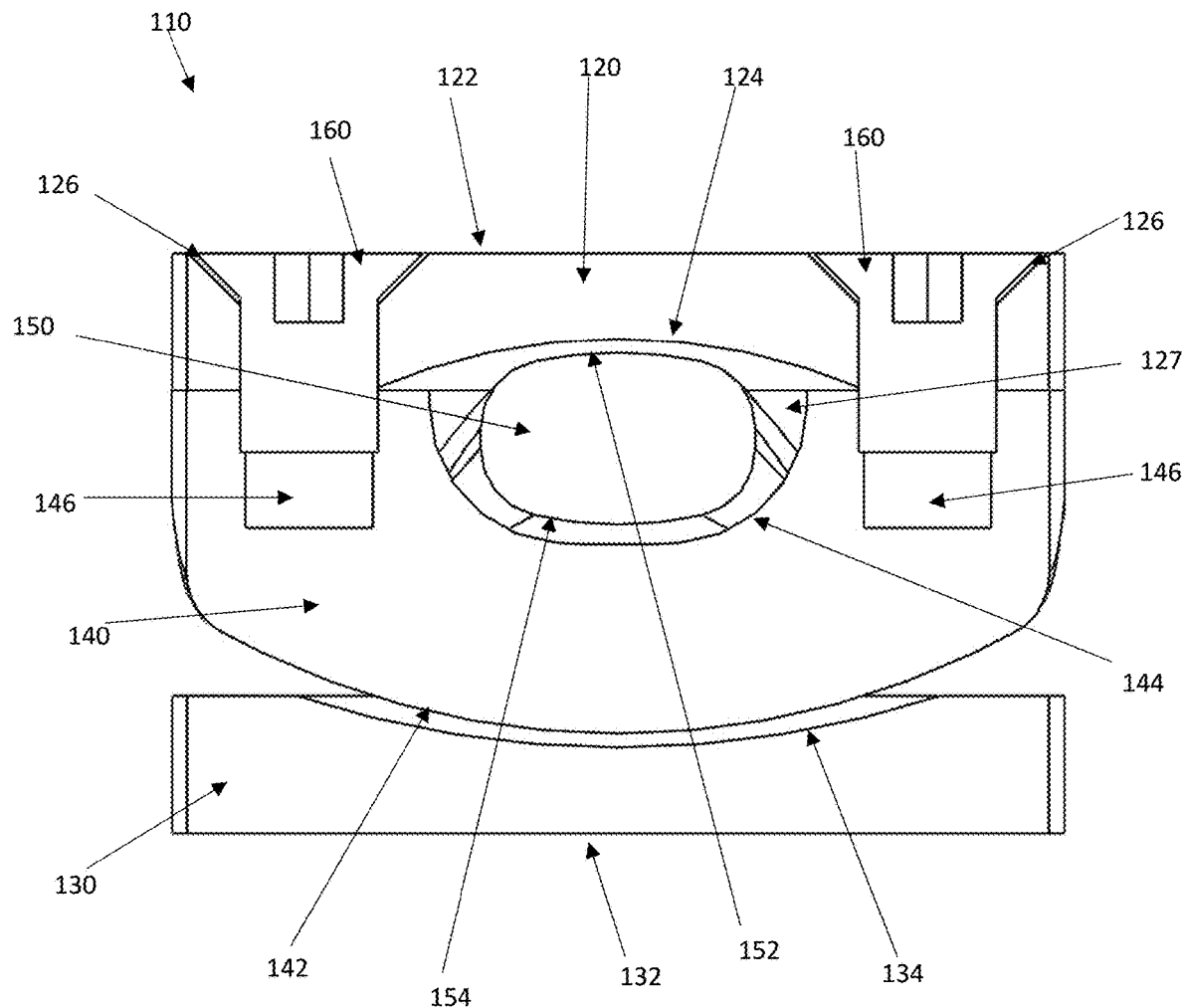
FIG. 13 is an anterior cross sectional view of an interlocking prosthetic spinal disc in accordance with a second embodiment of the present invention.

FIG. 13 is an anterior cross sectional view of an interlocking prosthetic spinal disc in accordance with a second embodiment of the present invention. In the depicted embodiment, an aperture 137 is disposed between the second u-shaped element 150 and the interior surface of the second base 135. In the depicted example, the aperture 137 is configured to receive the first u-shaped element 140.

Figure 14:
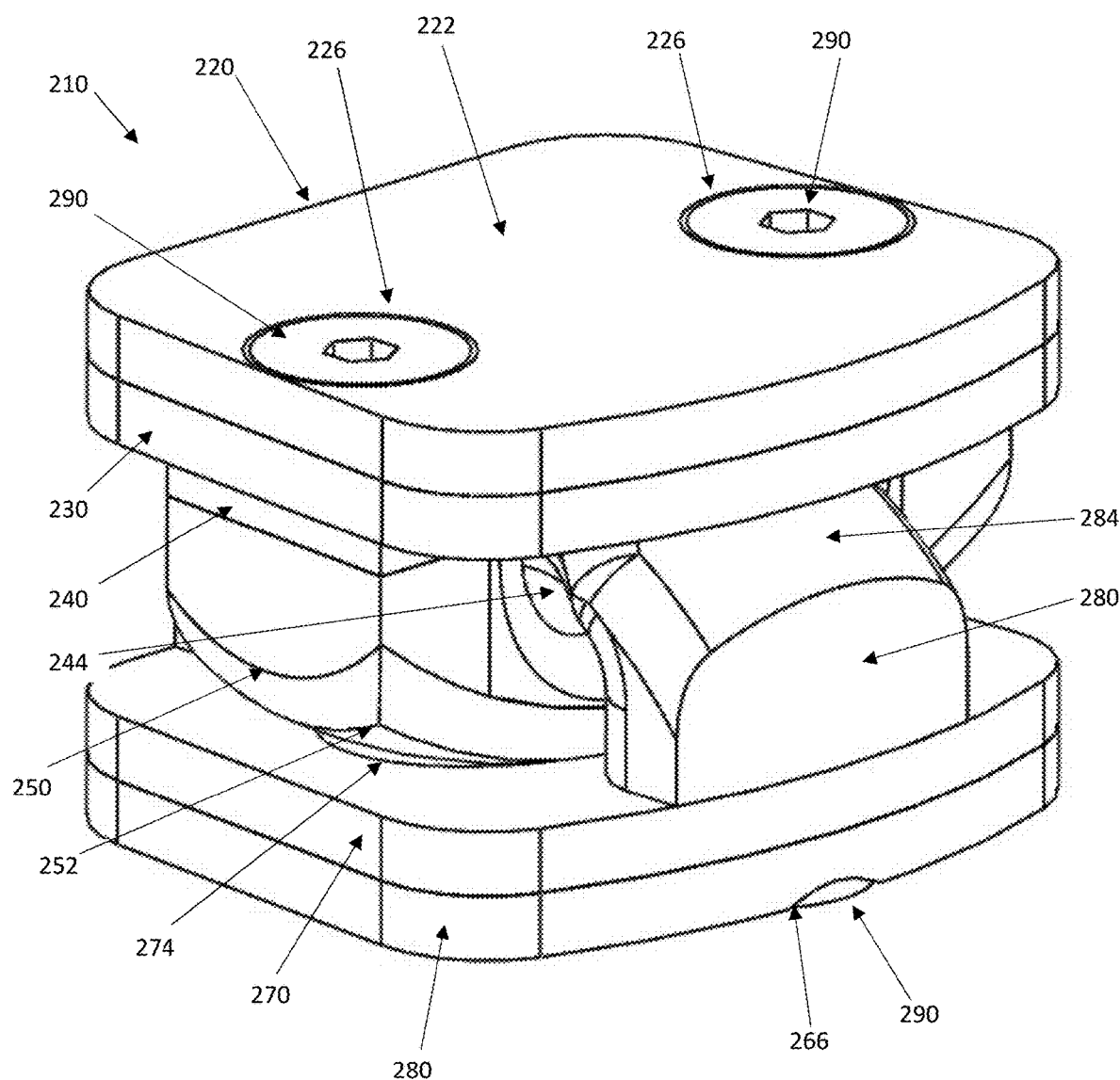
FIG. 14 is a perspective view of an interlocking prosthetic spinal disc in accordance with a third embodiment of the present invention.

Third Exemplary Embodiment:

FIG. 14 is a perspective view of a prosthetic spinal disc in accordance with a third embodiment of the present invention. In the depicted example, the prosthetic spinal disc 210 is comprised of a first base 225 and a second base 235. In the illustrated embodiment, the first base 225 is comprised of an interior endplate component 230 and an exterior endplate component 220. In the depicted example, the exterior endplate component 220 is configured to couple with the interior endplate component 230. Similarly, in the illustrated embodiment, the second base 235 is comprised of an interior endplate component 270 and an exterior endplate component 260. In the depicted example, the exterior endplate component 260 is configured to couple with the interior endplate component 270. In some embodiments, at least one of the exterior endplate component 220, the interior endplate component 230, the exterior endplate component 260, or the interior endplate component 270 are formed of ultra-high-molecular-weight polyethylene (UHMWPE) material. One of ordinary skill in the art would appreciate that there are numerous suitable and advantageous materials for creating endplate components 220, 230, 260, and 270, including other elastomeric materials, metal or ceramic, depending on the specific intended use application of the particular prosthetic spinal discs, and embodiments of the present invention are contemplated for use with any such materials.

Figure 15:
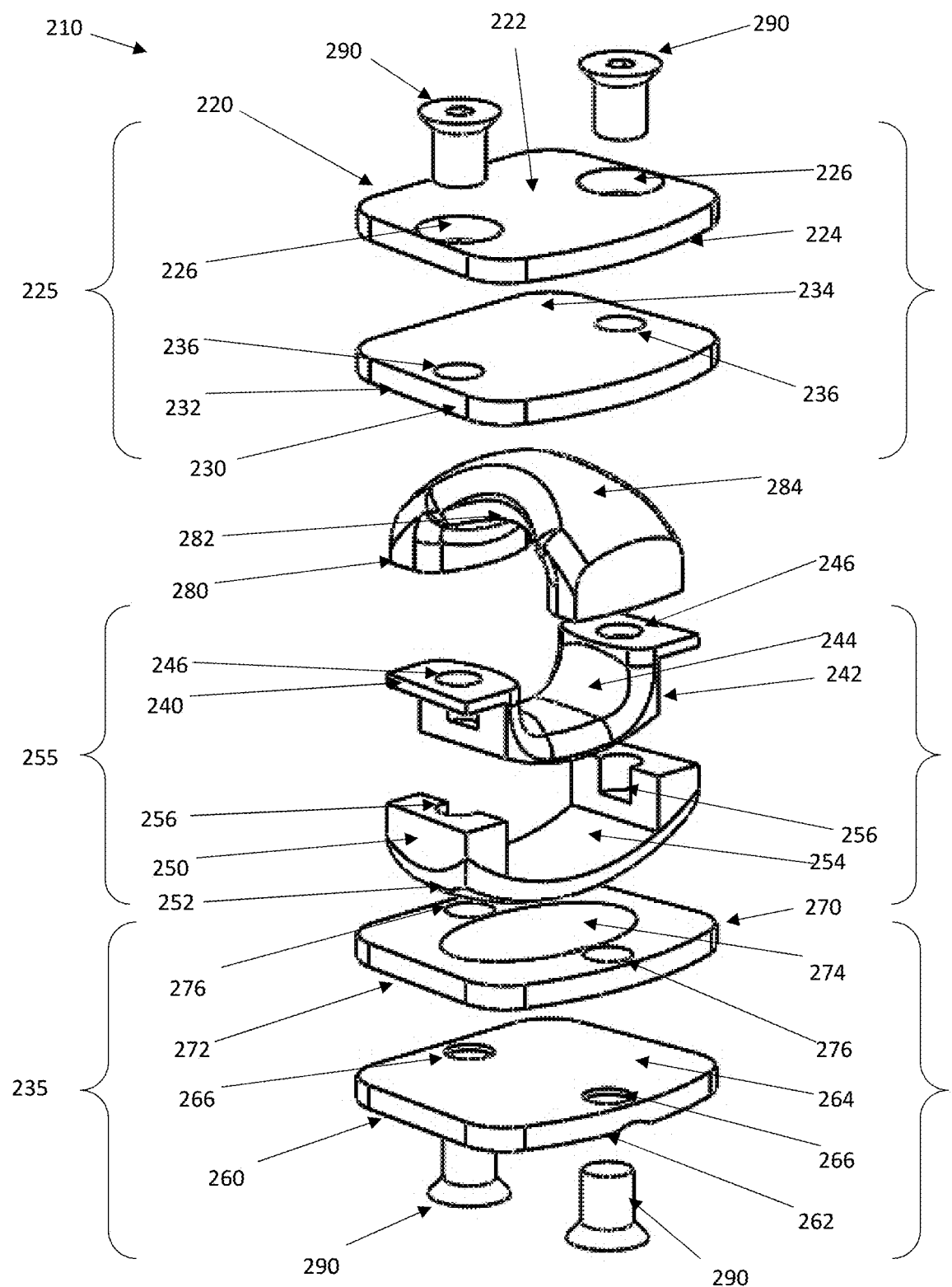
FIG. 15 is an exploded view of an interlocking prosthetic spinal disc in accordance with a third embodiment of the present invention.

FIG. 15 is an exploded view of an interlocking prosthetic spinal disc in accordance with a third embodiment of the present invention. In the illustrated embodiment, a first u-shaped element 255 is comprised of an inner u-shaped member 240 and an outer u-shaped member 250. In the depicted embodiment, the outer u-shaped member 250 is configured to receive the inner u-shaped member 240. In some embodiments, at least one of the inner u-shaped member 240 and the outer u-shaped member 250 are formed of UHMWPE material. In the depicted embodiment, the first u-shaped element 255 is configured to connect with the first base 225. In a preferred embodiment, the inner u-shaped member 240 connects to the interior endplate component 230 of the first base 225. In the depicted example, fasteners 290 connect the first u-shaped element 255 to the first base 225. In the illustrated embodiment, apertures 226 and 236 in the exterior endplate component 220 and the interior endplate component 230, respectively, are configured to receive fasteners 290 to secure the first u-shaped element 255 to the first base 225. In any embodiment, the fasteners 290 may be screws, pins, or any similar fastening members. In a preferred embodiment, the fasteners 290 connect the exterior endplate component 220 to the interior endplate component 230, the inner u-shaped element 240 and the outer u-shaped element 250. In the depicted embodiment, the inner u-shaped element 240 and the interior endplate component 230 are configured to be sandwiched between the exterior endplate component 220 and the outer u-shaped element 250.

As further shown in FIG. 15, in the illustrated embodiment, a second base 235 is comprised of an interior endplate component 270 and an exterior endplate component 260. In the depicted example, the exterior endplate component 260 is configured to couple with the interior endplate component 270. In some embodiments, at least one of the exterior endplate component 260 and the interior endplate component 270 are formed of UHMWPE material. In the depicted embodiment, a second u-shaped element 280 is configured to connect with the second base 235. In the depicted example, fasteners 290 connect the second u-shaped element 280 to the first base 235. In any embodiment, the fasteners 290 may be screws, pins, or any similar fastening members. In the illustrated example, the first u-shaped element 255 is configured to trap the second u-shaped element 280 between itself and the interior endplate component 230. Likewise, in the depicted example, the second u-shaped element 280 is configured to trap the first u-shaped element 255 between itself and the interior endplate component 270. In some examples, the first u-shaped element 255 is configured to articulate between the second u-shaped element 280 and the interior endplate component 270. Similarly, in some scenarios, the second u-shaped element 280 is configured to articulate between the first u-shaped element 255 and the interior endplate component 230. One of ordinary skill in the art would appreciate that there are numerous suitable and advantageous materials for creating the u-shaped elements 255 and 280, including other elastomeric materials, metal or ceramic, depending on the specific intended use application of the particular prosthetic spinal discs, and embodiments of the present invention are contemplated for use with any such materials.

In some examples, the exterior endplate component 220 includes a vertebral mating surface 222 on its exterior face. In some scenarios, the interior face of the exterior endplate component 220 includes an interior endplate component mating surface 224, configured to mate the exterior endplate component 220 to the interior endplate component 230. In some embodiments, the interior endplate component mating surface 224 is a UHMWPE mating surface. In some embodiments, the interior endplate component mating surface 224 may be generally flat, but configured to grip, by means of a roughened surface or adhesive, the interior endplate component 230. The exterior endplate component 220 may include one or more apertures 126 configured to receive fasteners 290. In some examples, the vertebral mating surface 222 may include spikes, teeth, porous areas, and similar texture and surface options which provide for improved mating with vertebral bodies. In some embodiments, the exterior endplate component 220 may be comprised of a metal such as stainless steel or cobalt chrome alloy. One of ordinary skill in the art would appreciate that there are numerous suitable and advantageous arrangements for endplate components 220, 230, 260, and 270 depending on the specific intended use application of the particular prosthetic spinal discs and embodiments of the present invention are contemplated for use with any such prosthetic spinal disc arrangements.

In some scenarios, the interior face of the interior endplate component 230 includes an exterior endplate component mating surface 234, configured to mate the interior endplate component 230 to the exterior endplate component 220. In some examples, opposite of the exterior endplate component mating surface 234 of the interior endplate component 230, is a base articulation surface 232. In some embodiments, the base articulation surface 232 may be flat. In some embodiments, the base articulation surface 232 may be concave. In some examples, the interior endplate component 230 includes one or more apertures 136 configured to receive fasteners 290.

Figure 16:
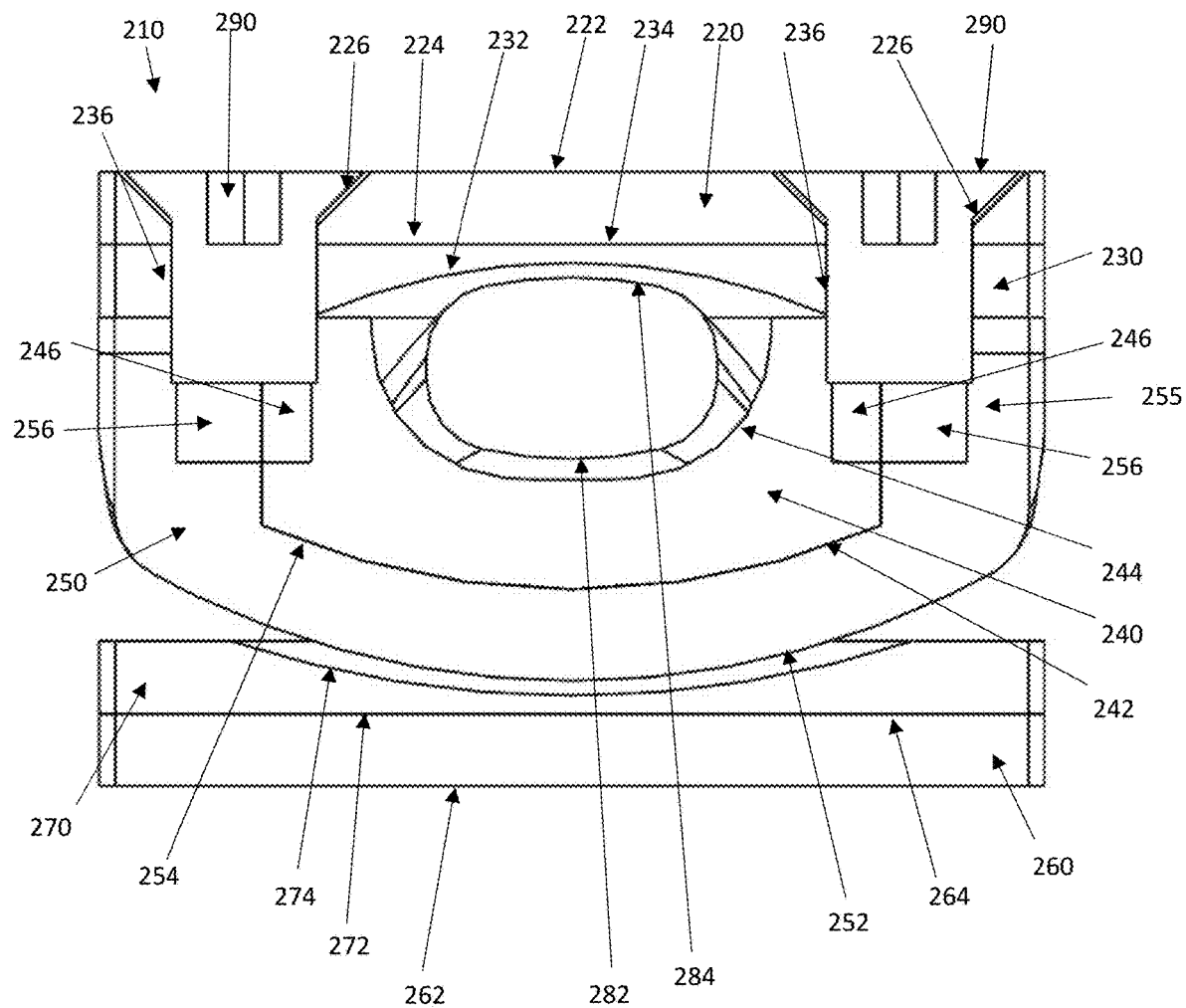
FIG. 16 is an anterior cross sectional view of an interlocking prosthetic spinal disc in accordance with a third embodiment of the present invention.

FIG. 16 is an anterior cross sectional view of an interlocking prosthetic spinal disc in accordance with a third embodiment of the present invention. In the illustrated embodiment, the first u-shaped element 255 is configured to connect and couple with the first base 225. In the depicted example, the interior endplate component 230 is disposed between the first u-shaped element 255 and the exterior endplate component 220. In the depicted example, apertures 226 and 236 of the exterior endplate component 220 and the interior endplate component 230, respectively, are configured to receive fasteners 290 to secure the first u-shaped element 255 to the first base 225. In the depicted example, the first u-shaped element 255 is configured to rest and articulate against the base articulation surface 274 of the interior endplate component 270. In some embodiments, the first u-shaped element 255 comprises an exterior articulating surface 252 and an interior articulating surface 244. In some embodiments, the exterior articulating surface 252 is generally convex. In some embodiments, the interior articulating surface 244 is generally concave. In some examples, the first u-shaped element 255 extends from one side of the first base 225 to a second side of the base 225.

Figure 17:
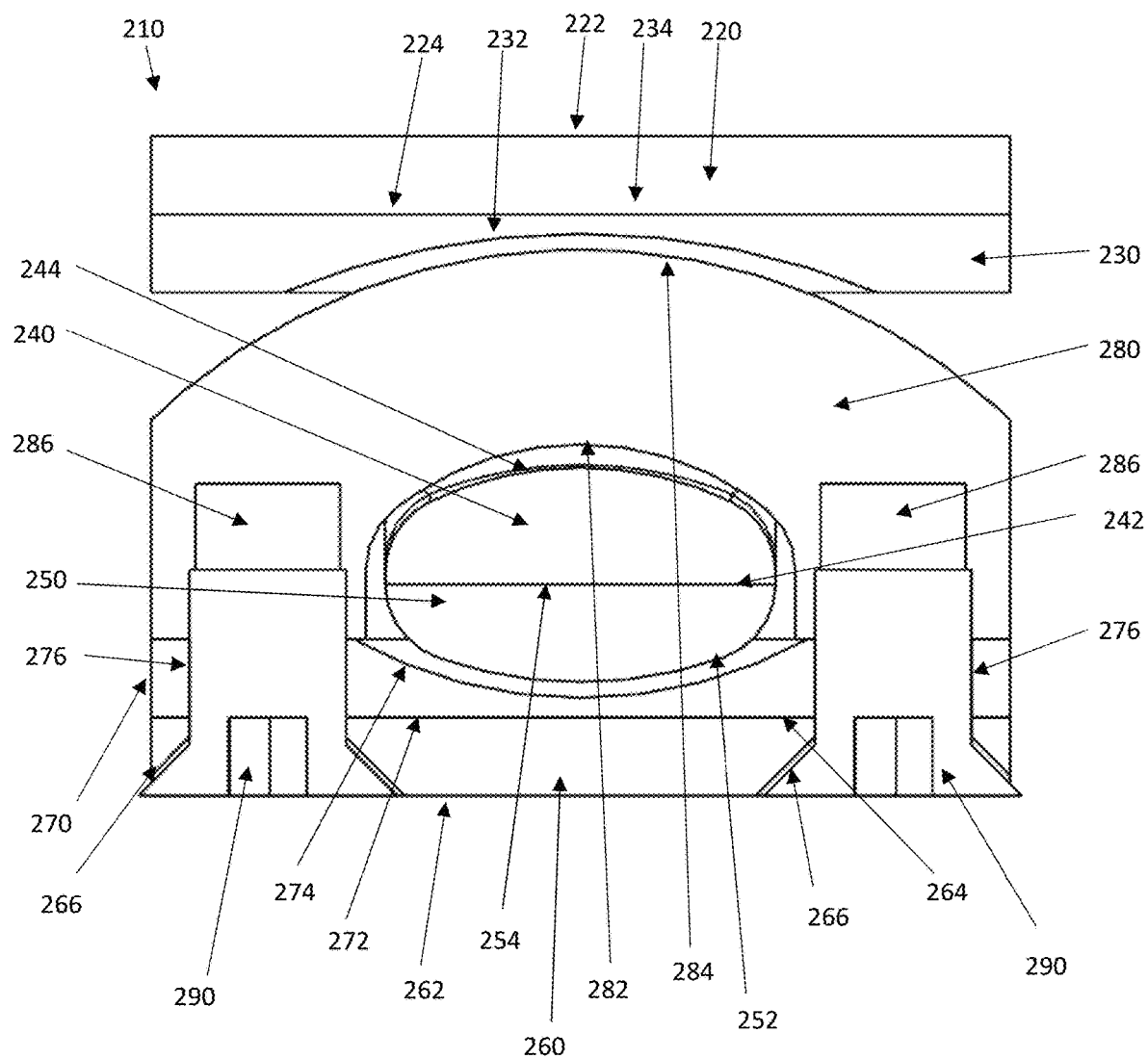
FIG. 17 is a lateral cross sectional view of an interlocking prosthetic spinal disc in accordance with a third embodiment of the present invention.

FIG. 17 is a lateral cross sectional view of an interlocking prosthetic spinal disc in accordance with a third embodiment of the present invention. In the illustrated embodiment, the second u-shaped element 280 is configured to connect and couple with the second base 235. In the depicted example, the interior endplate component 270 is disposed in between the exterior endplate component 260 and the second u-shaped element 280. In the depicted example, apertures 266 and 276 of the exterior endplate component 260 and the interior endplate component 270 are configured to receive fasteners 290 to secure the second u-shaped element 280 to the second base 235. In the depicted example, the second u-shaped element 280 is configured to rest and articulate against the base articulation surface 232 of the interior endplate component 230. In some embodiments, the second u-shaped element 280 comprises an exterior articulating surface 284 and an interior articulating surface 282. In some embodiments, the exterior articulating surface 284 is generally convex. In some embodiments, the interior articulating surface 282 is generally concave. In some examples, the second u-shaped element 280 generally extends from one side of the second base 235 to a second side of the base 235. In some embodiments, the first u-shaped element 255 and the second u-shaped element 280 may be comprised of a polyethylene material or a metal such as stainless steel or cobalt chrome alloy. One of ordinary skill in the art would appreciate that there are numerous suitable and advantageous materials for creating the u-shaped elements 255 and 280, depending on the specific intended use application of the particular prosthetic spinal discs and embodiments of the present invention are contemplated for use with any such materials.

In an example illustrative of the design and operation of various embodiment implementations, the interlocking prosthetic spinal disk 220 is assembled with the first u-shaped element 255 mated with the second u-shaped element 280. The two u-shaped elements 255 and 280 are configured to fasten to their corresponding bases 225 and 235, respectively, by fasteners 290. In some examples, the exterior articulating surface 252 of the first u-shaped element 255 is configured to rest and articulate on the base articulation surface 274 of the interior endplate component 270. Similarly, in some scenarios, the base articulation surface 232 of the interior endplate component 230 is configured to rest and articulate on the exterior articulating surface 284 of the second u-shaped element 280.

In some examples, the interior articulating surface 144 of the first u-shaped element 255 is configured to connect with the interior articulating surface 282 of the second u-shaped element 280. In an illustrative example, the interior articulating surface 244 of the first u-shaped element 255 is configured to articulate against the interior articulating surface 282 of the second u-shaped element 280. In various embodiments, the u-shaped element 255 of the first base 225 and the u-shaped element 280 of the second base 235 interlock with one another, preventing the two components from separating.

In another example illustrative of the design and operation of various embodiment implementations, the interlocked u-shaped elements 255 and 280 prevent over extension of the vertebral joint once the prosthetic spinal disc 210 is implanted. Moreover, the opposing orientation of the first u-shaped element 255 and the second u-shaped element 280 prevents over-rotation of each of the first and second bases 225 and 235, respectively. In an illustrative example, the second u-shaped element 280 and the first u-shaped element 255 are configured to rest against and limit the movement of one another as the prosthetic spinal disc 210 articulates, rotates or moves with the joint.

Figure 18:
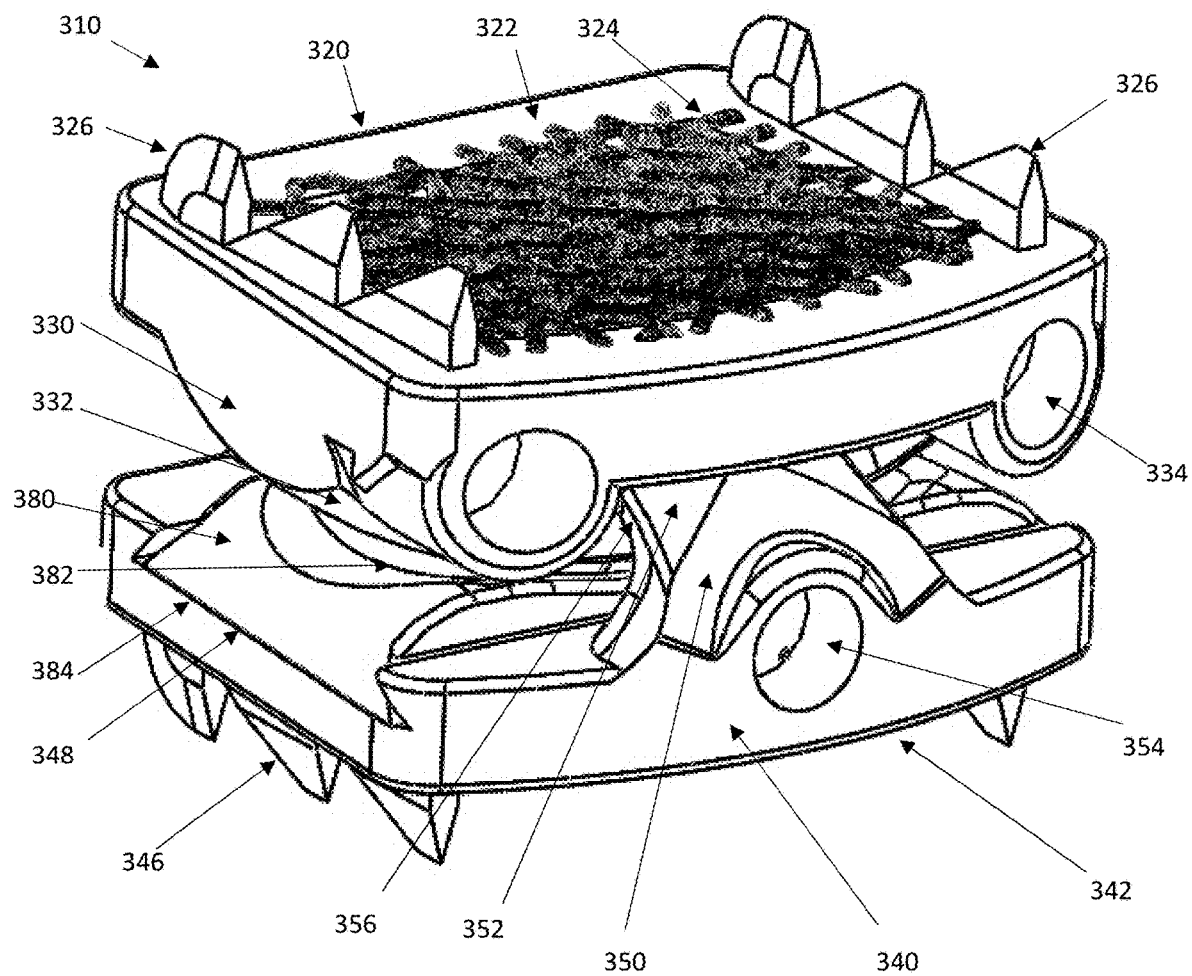
FIG. 18 is a perspective view of an interlocking prosthetic spinal disc in accordance with a fourth embodiment of the present invention.

Fourth Exemplary Embodiment:

FIG. 18 is a perspective view of an interlocking prosthetic spinal disc in accordance with a fourth embodiment of the present invention. In the illustrated embodiment, the interlocking prosthetic spinal disc 310 is comprised of a first endplate component 320 and a second endplate component 340. In the illustrated example, the first endplate component 320 and the second endplate component 340 include fastening apertures 334. In any embodiment, one or more fastening apertures 334 may be disposed on either or both of the first and second endplate components 320 and 340. The fastening apertures 334 are configured to receive and engage with a fastener (not shown) in order to secure the disc 310 to bone. In the depicted embodiment, the first endplate component 320 and the second endplate component 340 each include a vertebral mating surface 322 and 342, respectively, on an exterior portion of the component. In the illustrated embodiment, the vertebral mating surface 322 includes a porous bone ingrowth surface 324 to promote bone mating and growth. In the depicted embodiment, the vertebral mating surface 322 of the first endplate component 320 and the vertebral mating surface 342 of the second endplate component 340 each include a plurality of keels 326. In any embodiment, the vertebral mating surfaces 322 and 342 may include one or more keels 326. The keels 326 are configured to cut into vertebral bodies. In some embodiments, the keels 326 may be configured as teeth or any other feature to cut into the vertebral bodies to prevent migration. One of ordinary skill in the art would appreciate that there are numerous suitable and advantageous arrangements for the keels depending on the specific intended use application of the particular prosthetic spinal implant and embodiments of the present invention are contemplated for use with any such prosthetic spinal implant arrangements.

Figure 19:
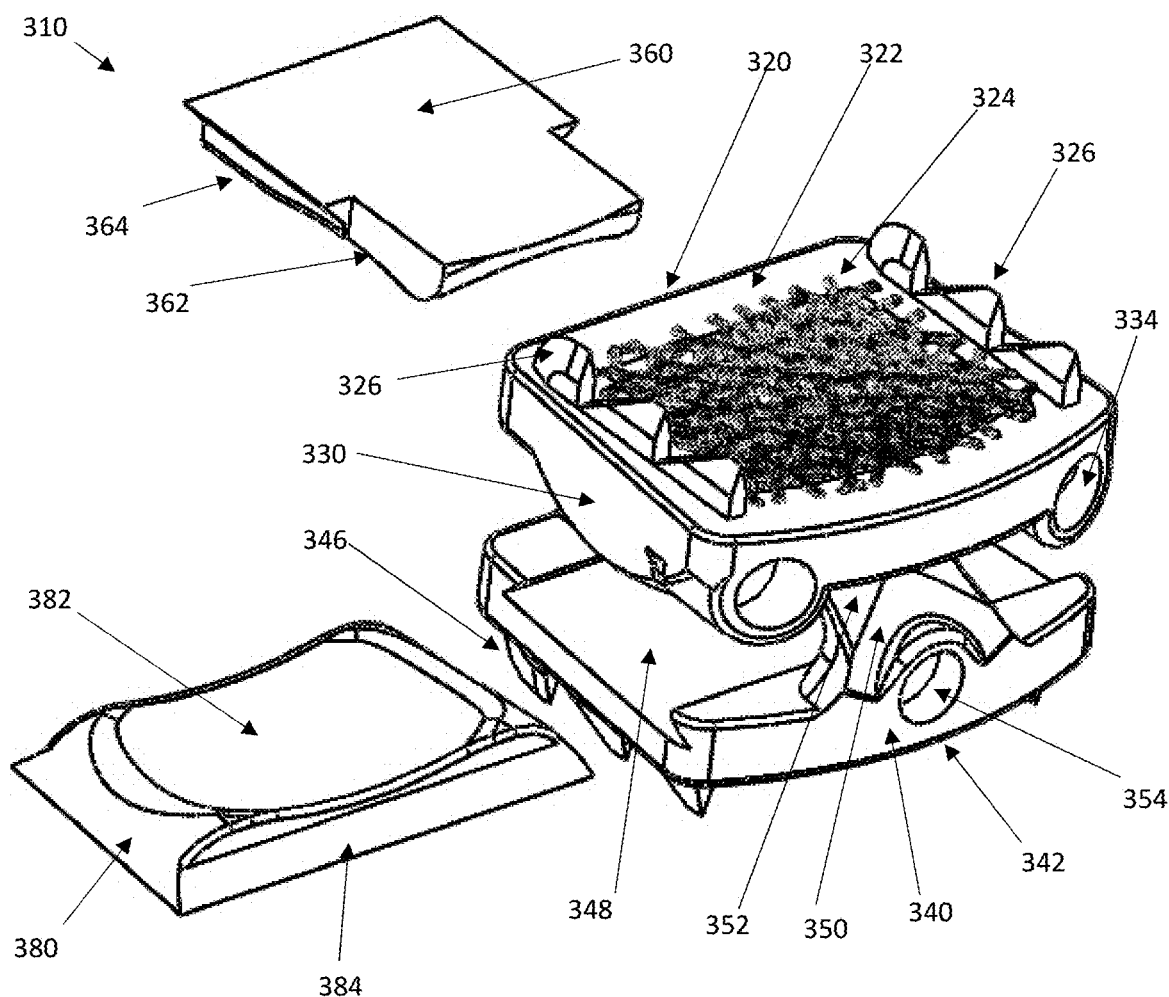
FIG. 19 is a partially unassembled view of an interlocking prosthetic spinal disc in accordance with a fourth embodiment of the present invention.

FIG. 19 is a partially unassembled view of an interlocking prosthetic spinal disc in accordance with a fourth embodiment of the present invention. In the illustrated example, the interlocking prosthetic spinal disc 310 is comprised of a first endplate component 320 and a second endplate component 340. In the depicted example, the first endplate component 320 comprises a first base 325, a first platform component 360, and a first u-shaped element 330. Similarly, in the illustrated example, the second endplate component comprises a second base 335, a second platform component 380, and a second u-shaped element 350. In some embodiments, the u-shaped elements 330 and 350 are flexible. In some embodiments, the u-shaped elements 330 and 350 are configured to selectively deform. In some examples, the first platform component 360 is configured to slidably engage with and lock into the first endplate component 320. Similarly, in some embodiments, the second platform component 380 is configured to slidably engage with and lock into the second endplate component 340. In the depicted example, the first platform component 360 includes a base articulation surface 362 configured to articulate against the exterior articulating surface 352 of the second endplate component 340. In the illustrated example, the base articulation surface 362 is generally convex. In some embodiments, any of the bases 325 and 335, the platform components 360 and 380, and the u-shaped elements 330 and 350 may be formed of a UHMWPE material. One of ordinary skill in the art would appreciate that there are numerous suitable and advantageous materials for creating the bases 325 and 335, the platform components 360 and 380, and the u-shaped elements 330 and 350, including other elastomeric materials, metal or ceramic, depending on the specific intended use application of the particular prosthetic spinal discs, and embodiments of the present invention are contemplated for use with any such materials.

Figure 20:
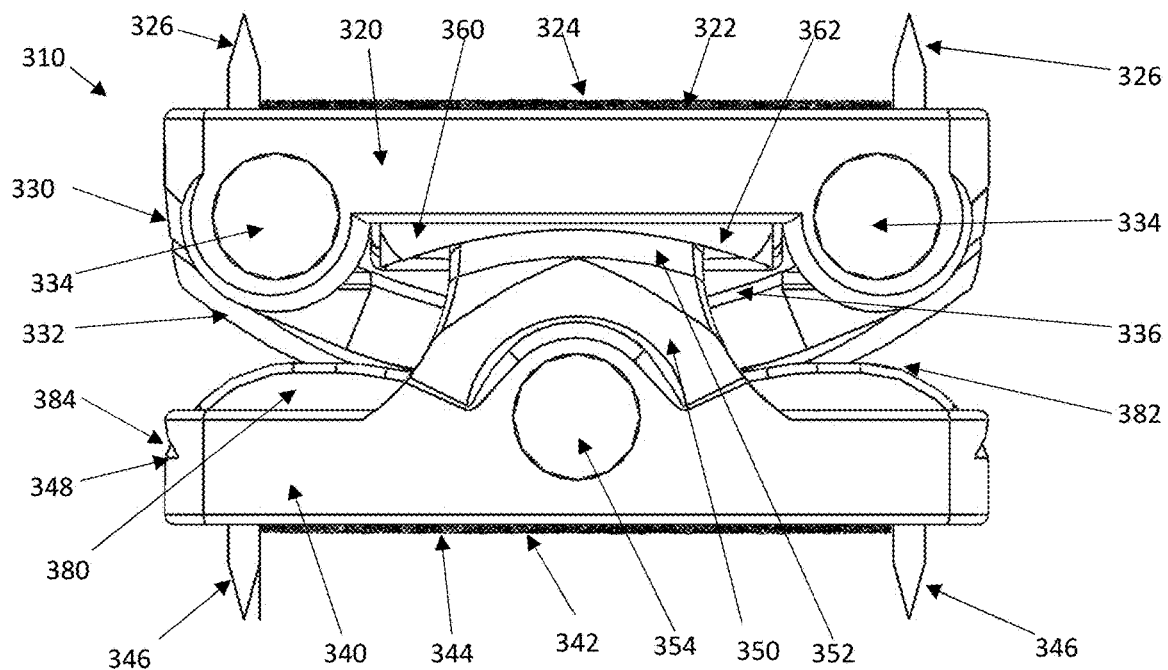
FIG. 20 is an anterior view of an interlocking prosthetic spinal disc in accordance with a fourth embodiment of the present invention.
Figure 21:
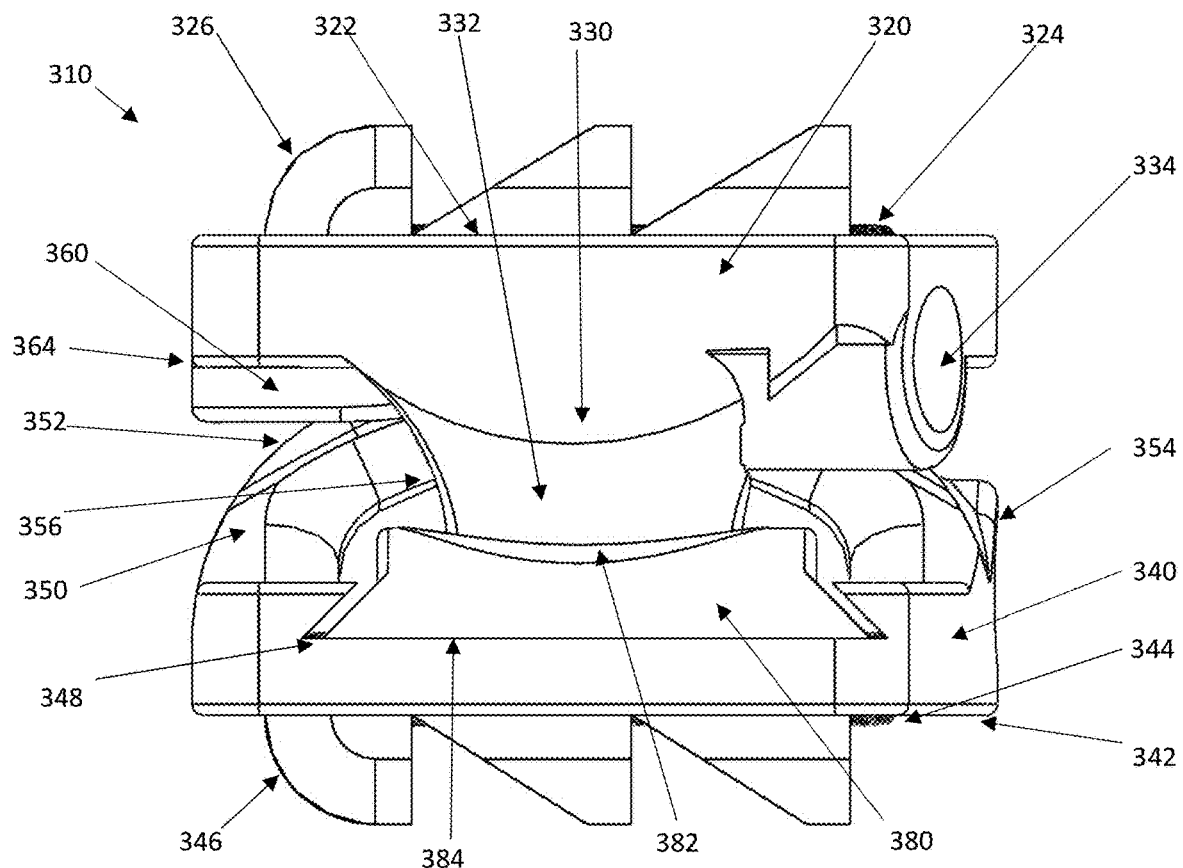
FIG. 21 is a lateral view of an interlocking prosthetic spinal disc in accordance with a fourth embodiment of the present invention.

FIGS. 20 and 21 depict an interlocking prosthetic spinal disc in accordance with a fourth embodiment of the present invention. In the illustrated embodiment, the vertebral mating surface 342 includes a porous bone ingrowth surface 344. In some embodiments, the first platform component 360 is configured to slide between the first endplate component 320 and the exterior articulating surface 352 of the second endplate component 340. In some embodiments, an interior portion of the first base 325 may be dove-tailed to accept the first platform component 360. In the illustrated embodiment, extending from the first base 325 is the u-shaped element 330 comprising an exterior articulating surface 332 and an interior articulating surface 336. In the depicted example, the exterior articulating surface 332 is generally convex and the interior articulating surface 336 is generally concave. In the illustrated example, the u-shaped element 330 of the first endplate component 320 extends from one side of the first base 325 to a second side of the base 325. In the depicted embodiment, the second platform mating surface 348 is disposed on the interior face of the second endplate component 340. In some embodiments, the second platform mating surface 348 may be dove-tailed to accept the second platform component 380. In the illustrated embodiment, extending from the second base 335 is the u-shaped element 350 comprising an exterior articulating surface 352 and an interior articulating surface 356. In the depicted example, the exterior articulating surface 352 is generally convex and the interior articulating surface 356 is generally concave. In the illustrated example, the u-shaped element 350 of the second endplate component 340 extends from a first side of the second base 335 to a second side of the base 335.

Figure 22:
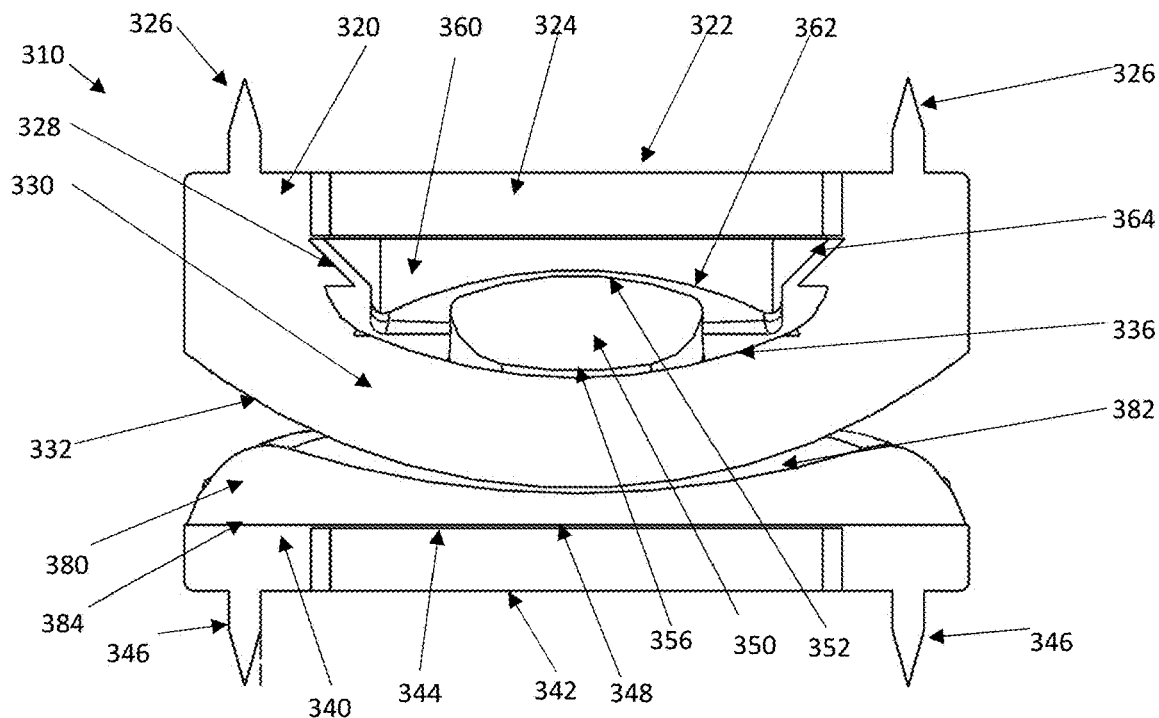
FIG. 22 is an anterior cross sectional view of an interlocking prosthetic spinal disc in accordance with a fourth embodiment of the present invention.
Figure 23:
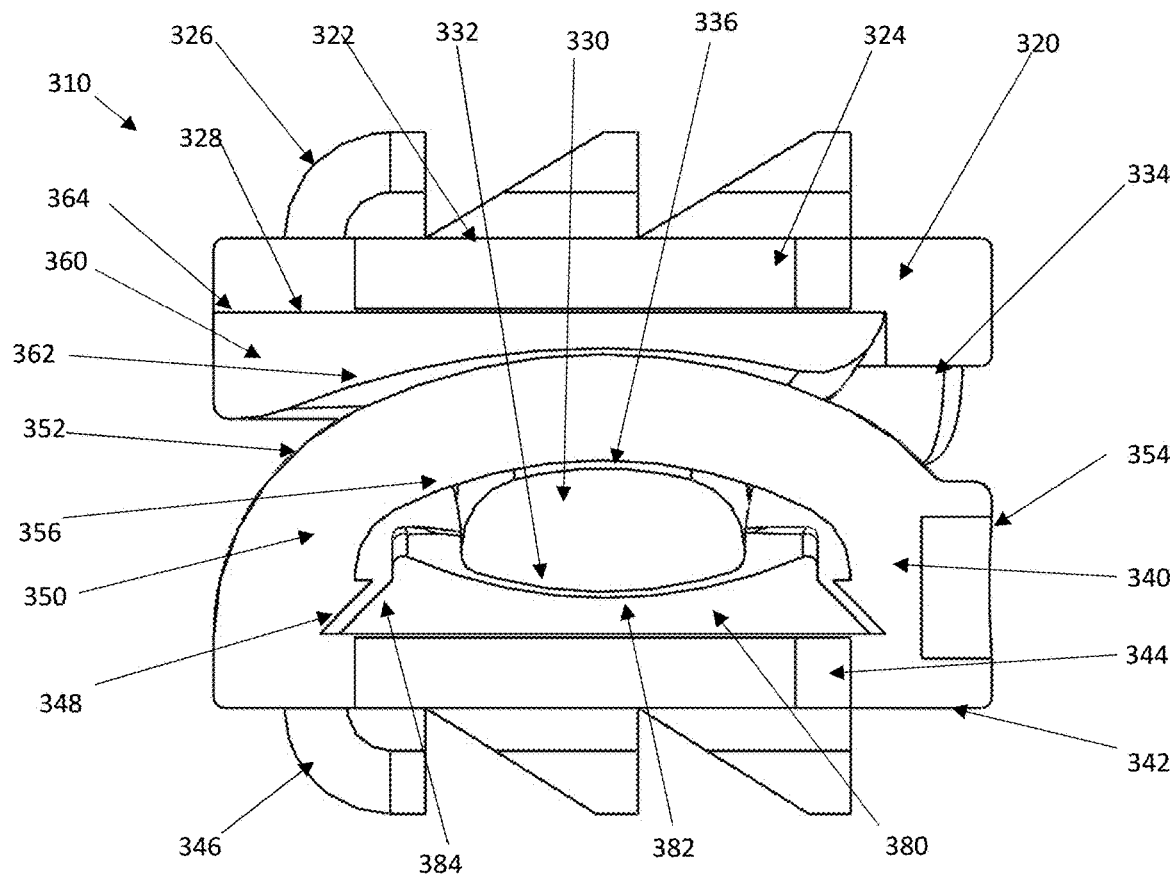
FIG. 23 is a lateral cross sectional view of an interlocking prosthetic spinal disc in accordance with a fourth embodiment of the present invention.

FIGS. 22 and 23 depict an interlocking prosthetic spinal disc in accordance with a fourth embodiment of the present invention. In the depicted example, the second endplate component 340 includes one or more fastening apertures 354. In the illustrated example, the first platform component 360 includes an endplate mating surface 364 configured with a locking mechanism to lock with the platform component mating surface 328 of the first endplate component 320. Similarly, in the illustrated embodiment, the second platform component 380 includes an endplate mating surface 348 configured with a locking mechanism to lock with the platform mating surface 348 of the second endplate component 380. In some embodiments, the locking mechanism is a dovetail locking mechanism.

As shown in FIG. 22, the second platform component 380 may be configured to slide between the second endplate component 340 and the exterior articulating surface 332 of the first endplate component 320. In the illustrated embodiment, the second platform component 380 includes a base articulation surface 382 configured to articulate against the exterior articulating surface 332 of the first endplate component 320. In the depicted embodiment, the base articulation surface 382 is generally convex.

In an example illustrative of the design and operation of various embodiment implementations, the interlocking prosthetic spinal disc 310 may be 3D printed such that the first endplate component 320 is printed at the same time as the second endplate component 340. Therefore, the u-shaped element 330 of the first endplate component 320 and the u-shaped element 350 of the second endplate component 340 may be integrally formed, and printed simultaneously, so that they are interlocking with one another. In some scenarios, once the first endplate component 320 and second endplate component 340 are printed, the first platform component 360 and second platform component may be slid and locked into place. In some examples, the exterior articulating surface 332 of the first endplate component 320 is configured to rest and articulate on the base articulation surface 382 of the second platform component 380. Similarly, the base articulation surface 362 of the first platform component 360 is configured to rest and articulate on the exterior articulating surface 352 of the second endplate component 340.

In another example illustrative of the design and operation of various embodiment implementations, the interlocked u-shaped elements 330 and 350 prevent over extension of the vertebral joint once the prosthetic spinal disc 310 is implanted. Moreover, the opposing orientation of the u-shaped element 330 and the u-shaped element 350 prevents over-rotation of each of the first and second endplate components 320 and 340, respectively. In an illustrative example, the second u-shaped element 350 and the first u-shaped element 330 are configured to rest against and limit the movement of one another as the prosthetic spinal disc 310 rotates with the joint.

Figure 24:
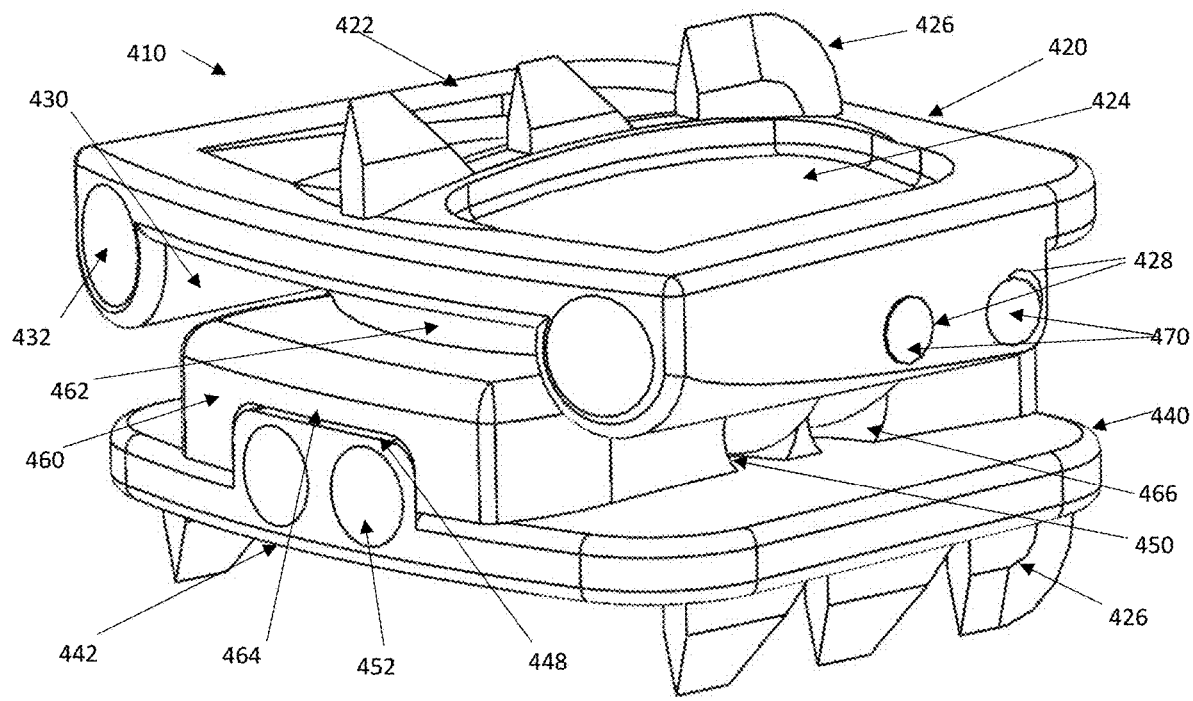
FIG. 24 is a perspective view of an interlocking prosthetic spinal disc in accordance with a fifth embodiment of the present invention.

Fifth Exemplary Embodiment:

FIG. 24 is a perspective view of an interlocking prosthetic spinal disc in accordance with a fifth embodiment of the present invention. In the illustrated embodiment, the interlocking prosthetic spinal disc 410 is comprised of a first endplate component 420, a second endplate component 440, an articulating element 460, and one or more connector rods 470. In some embodiments, the first endplate component 420 includes one or more elongate extensions 430. In the illustrated example, the first endplate component 420 includes two elongate extensions 430. In the depicted example, each elongate extension 430 includes an inserter aperture 432. In some embodiments, the inserter apertures 432 are configured to engage with an inserter (not shown). In some scenarios an inserter (not shown) is used to connect to and hold the disc 410 while the disc 410 is inserted into a patient body during a given procedure. In some embodiments, the elongate extensions 430 include rod apertures 428. In the illustrated embodiment, the rod apertures 428 are configured to correspond to the shape of the connector rods 470 and fasten the connector rods 470 to the first endplate component. In some examples, the elongate extensions 430 may be crimped or deformed to hold or secure the connector rods 470 in place. In some embodiments, the connector rods 470 may be connected and secured to the elongate extensions 430 using a fastener such as a screw, pin or similar fastening member. In the depicted embodiment, the first endplate component 420 and the second endplate component 440 each include a vertebral mating surface 422 and 442, respectively, on an exterior portion of the component. In the illustrated embodiment, the vertebral mating surface 422 includes a porous bone ingrowth surface 424 to promote bone mating and growth. In the depicted embodiment, the vertebral mating surface 422 of the first endplate component 420 and the vertebral mating surface 442 of the second endplate component 440 each include a plurality of keels 426. In any embodiment, the vertebral mating surfaces 422 and 442 may include one or more keels 426 configured to cut into vertebral bodies. In some embodiments, the keels 426 may be configured as teeth or any other feature to cut into the vertebral bodies to prevent migration.

Figure 25:
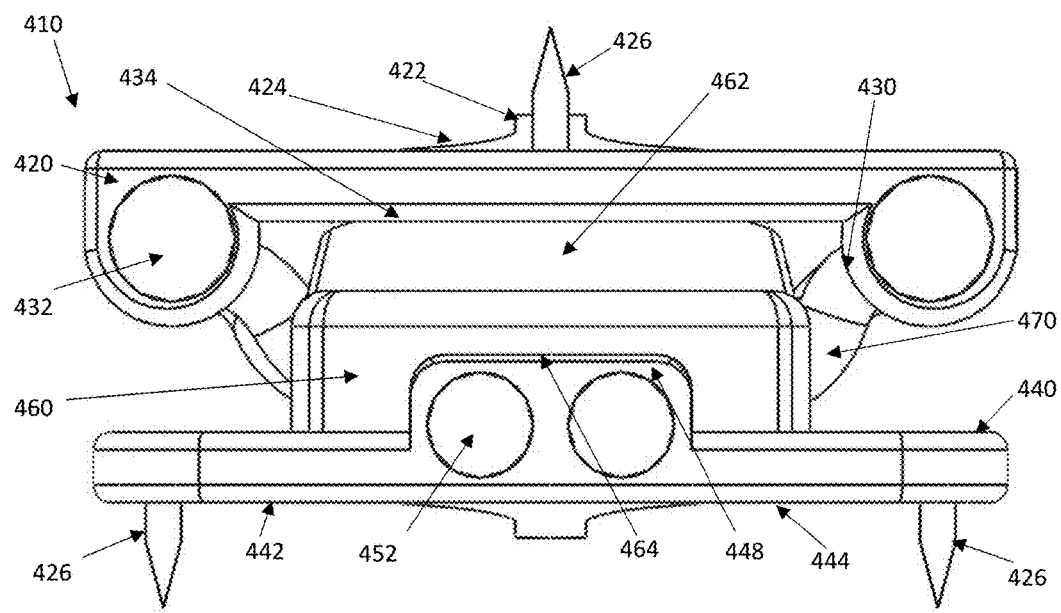
FIG. 25 is an anterior view of an interlocking prosthetic spinal disc in accordance with a fifth embodiment of the present invention.
Figure 26:
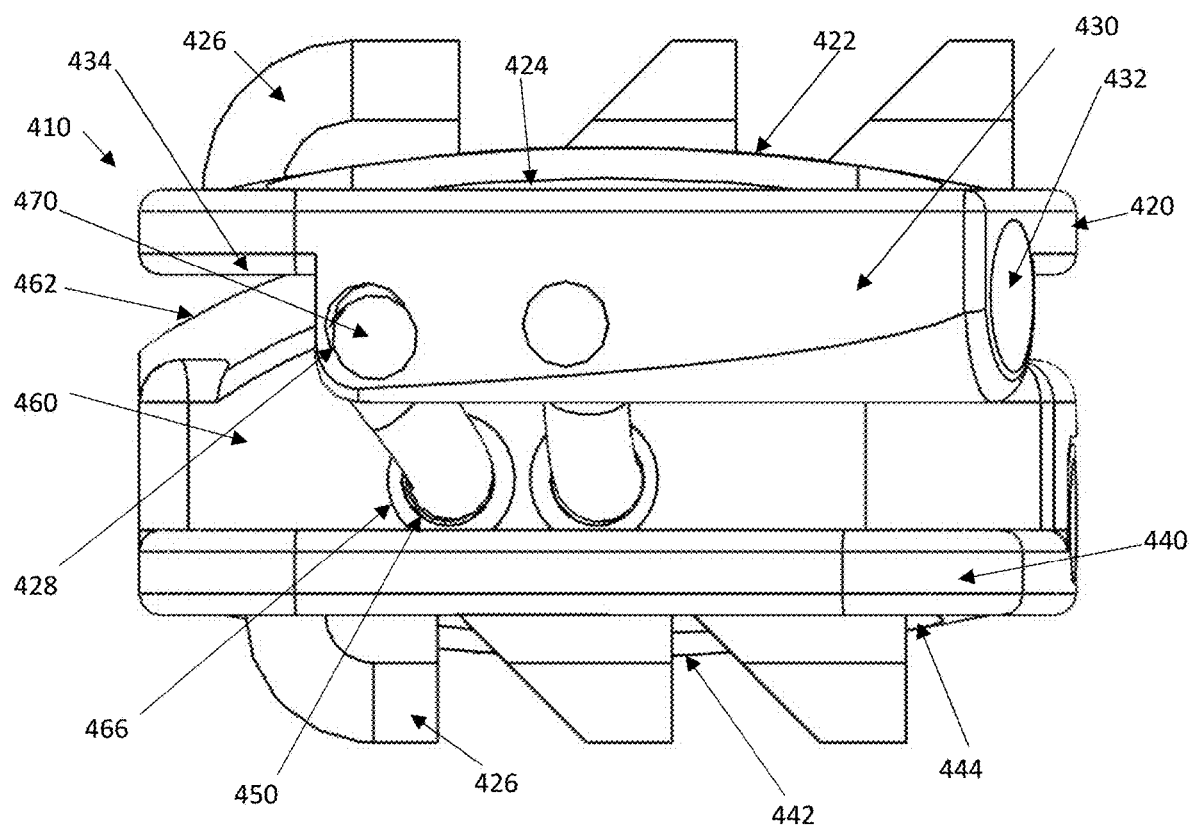
FIG. 26 is a lateral view of an interlocking prosthetic spinal disc in accordance with a fifth embodiment of the present invention.

FIGS. 25 and 26 depict an interlocking prosthetic spinal disc in accordance with a fifth embodiment of the present invention. In some embodiments, the vertebral mating surface 442 of the second endplate component 440 includes a porous bone ingrowth surface 444 to promote bone mating and growth. In some embodiments, the interior portion of the first endplate component 420 includes an articulating surface 434 and one or more connector rods 470. In some embodiments, the articulating surface 434 of the first endplate component 420 is generally concave. In the illustrated embodiment, two connector rods 470 extend from the first endplate component 420. In some embodiments, the connector rods 470 are flexible. In the depicted example, the two connector rods 470 of the first endplate component 420 each extend from one side of the first endplate component 420 to a second side of the first endplate component 420. In the illustrated embodiment, extending from the inner surface of the second endplate component 440 is a protruding platform 448 configured to connect to an articulating element 460. In some embodiments, the articulating element 460 has a substantially rectangular frame and is configured to protrude from the second endplate component 440 and includes an exterior articulating surface 462. In some embodiments, the exterior articulating surface 462 of the articulating element 460 is generally convex. In some embodiments, the articulating element 460 may have a generally round, oval, triangular or any other geometrically shaped frame. In some embodiments, the articulating element 460 includes one or more outer apertures 466 configured to receive one or more connector rods 470. In some embodiments, the protruding platform 448 includes one or more inner apertures 450 configured to receive one or more connector rods 470. In some embodiments, the articulating element 460 is formed of UHMWPE material. In the depicted example, the articulating element 460 includes a convex surface configured as an exterior articulating surface 462. In some embodiments, the exterior articulating surface 462 is substantially flat. In the depicted embodiment, the connector rods 470 extend across the articulating element 460, through outer apertures 466 and inner apertures 450. In some embodiments, the connector rods 470 are inserted through outer apertures 466 and inner apertures 450 to fasten the articulating element 460 to the second endplate component 440. In some embodiments, the apertures 450 and 466 are configured to allow one or more connector rods 470 to slightly move within the articulating element 460 while securing the articulating element 460 to the second endplate component 440. In some embodiments, the apertures 450 and 466, either alone or in combination, are configured to prevent the connector rods 470 from moving anterior-posterior or cephalad-caudal in relation to the second endplate component 440. One of ordinary skill in the art would appreciate that there are numerous suitable and advantageous arrangements for the articulating element depending on the specific intended use application of the particular interlocking prosthetic spinal disc and embodiments of the present invention are contemplated for use with any such prosthetic spinal disc arrangements.

In some embodiments, the connector rods 470 are comprised of a flexible material such as NiTiNol wire, UHMWPE fibers, or similar material. In some embodiments, the connector rods 470 are held securely at each end within the rod apertures 428 in the first endplate component 420. In some embodiments, a middle portion of each connector rod 470 is retained within inner apertures 450 disposed on the articulating element 460. In some embodiments, the connector rods 470 are configured to connect the first endplate component 420 to the second endplate component 440, while also holding the articulating element 460 substantially in place. In some embodiments, the flexibility of the connector rods 470 permits the first endplate component 420 to move and rotate with respect to the second endplate component 440, while substantially preventing over-rotation.

Figure 27:
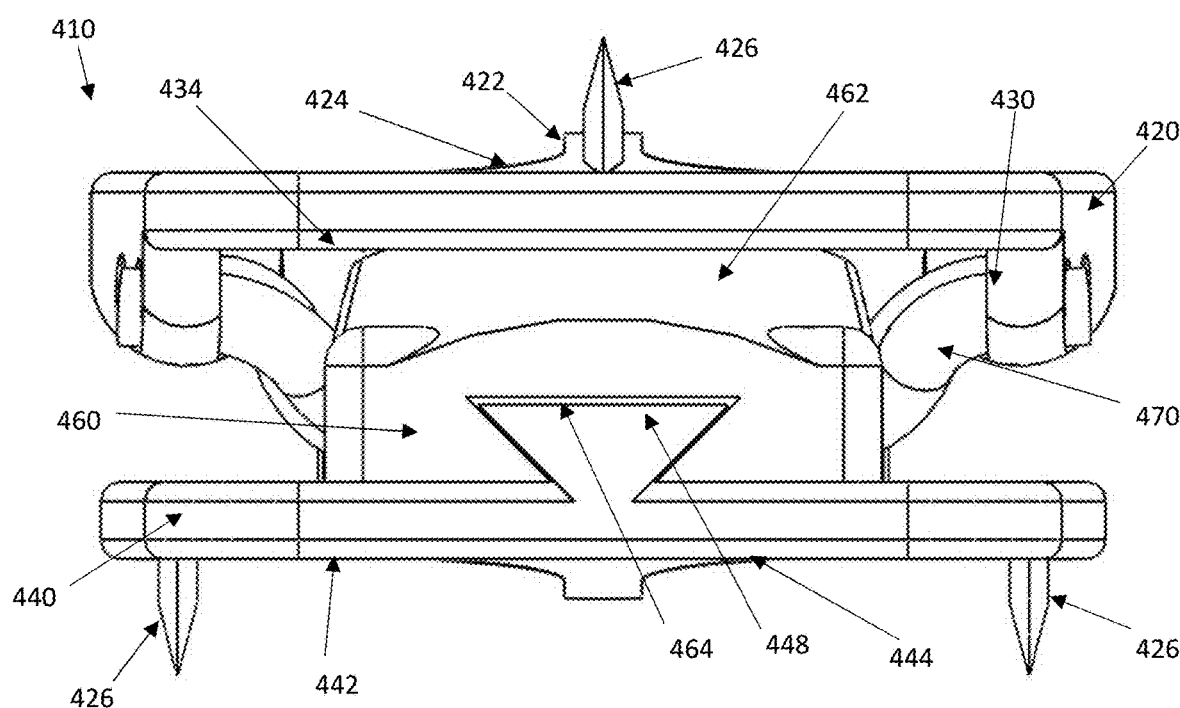
FIG. 27 is a cross sectional view of an interlocking prosthetic spinal disc in accordance with a fifth embodiment of the present invention.

FIG. 27 depicts a cross-sectional view of an interlocking prosthetic spinal disc in accordance with a fifth embodiment of the present invention. In some embodiments, the articulating element 460 includes an endplate mating means configured to fasten the articulating element 460 to the second endplate component 440. In the illustrated embodiment, the endplate mating means is an indentation 464 in the articulating element 460 configured to mate with the protruding platform 448 on the second endplate component 440. In the depicted embodiments, the indentation 464 and the protruding platform 448 are configured in corresponding dovetail orientations which are adapted to secure the articulating element 460 to the second endplate component 440. In the depicted example, the articulating element 460 is disposed between the first endplate component 420 and the second endplate component 440. In some embodiments, the articulating element 460 includes an articulation surface 462 configured to rest or articulate against the articulating surface 434 of the first endplate component 420.

FIG. 28 depicts a perspective view of an interlocking prosthetic spinal disc in accordance with a sixth embodiment of the present invention. In the illustrated embodiment, the interlocking prosthetic spinal disc 510 is comprised of a first endplate component 520, a second endplate component 540, an articulating element 560, and one or more connector rods 570. In some embodiments, the first endplate component 520 includes one or more elongate extensions 530. In the illustrated example, the first endplate component 520 includes two elongate extensions 530. In the depicted example, each elongate extension 530 includes an inserter aperture 532. In some embodiments, the inserter apertures 532 are configured to engage with an inserter (not shown). In some scenarios an inserter (not shown) is used to insert the disc 510 into a patient body during a given procedure. In some embodiments, the elongate extensions 530 include rod apertures 528. In the illustrated embodiment, the rod apertures 528 are configured to correspond to the shape of the connector rods 570 and fasten the connector rods 570 to the first endplate component 520. In the depicted embodiment, the first endplate component 520 and the second endplate component 540 each include a vertebral mating surface 522 and 542, respectively, on an exterior portion of the component. In the illustrated embodiment, the vertebral mating surface 522 includes a porous bone ingrowth surface 524 to promote bone mating and growth. In the depicted embodiment, the vertebral mating surface 522 of the first endplate component 520 and the vertebral mating surface 542 of the second endplate component 540 each include a plurality of keels 526. In any embodiment, the vertebral mating surfaces 522 and 542 may include one or more keels 526 configured to cut into vertebral bodies. In some embodiments, the keels 526 may be configured as teeth or any other feature to cut into the vertebral bodies to prevent migration.

Figure 31:
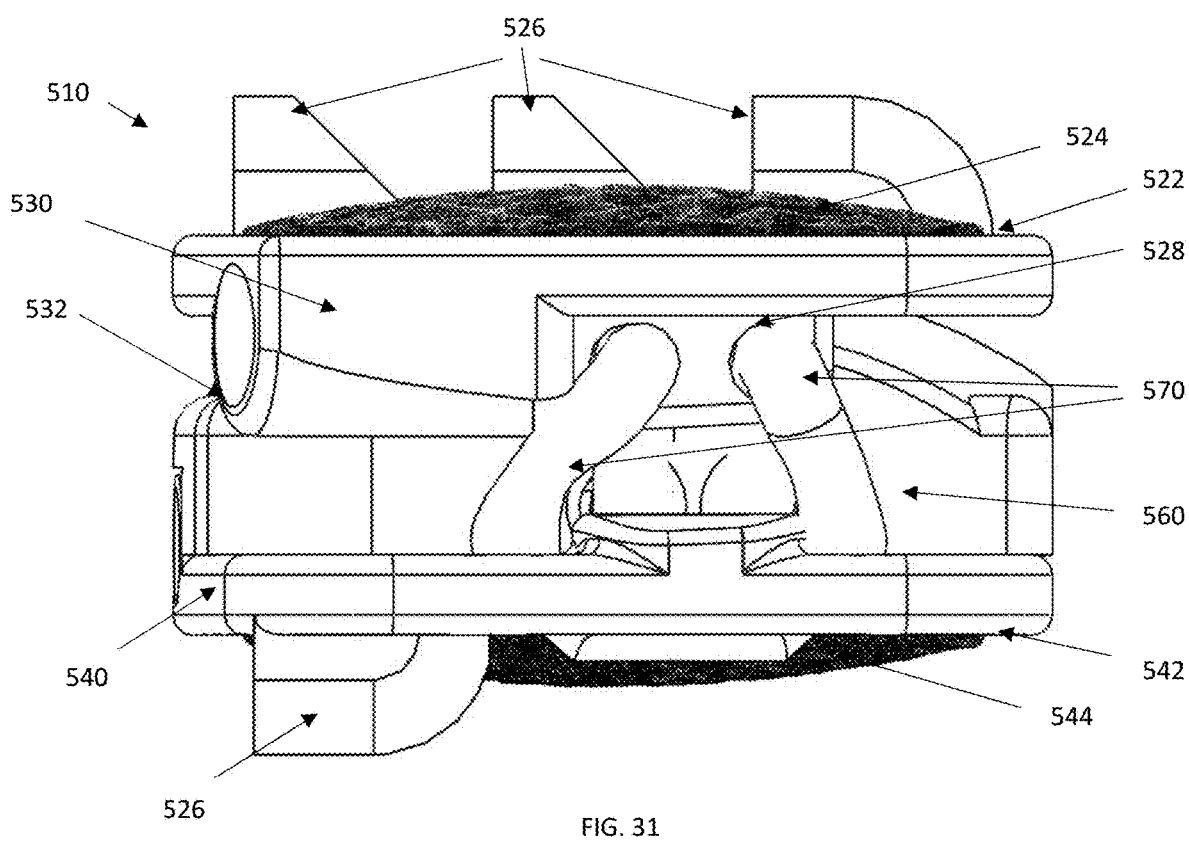
FIG. 31 is a lateral view of an interlocking prosthetic spinal disc in accordance with a sixth embodiment of the present invention.

FIGS. 29 and 31 depict an interlocking prosthetic spinal disc in accordance with a sixth embodiment of the present invention. In some embodiments, the vertebral mating surface 542 of the second endplate component 540 includes a porous bone ingrowth surface 544 to promote bone mating and growth. In some embodiments, the interior portion of the first endplate component 520 includes an articulating surface 534 and one or more connector rods 570. In some embodiments, the articulating surface 534 of the first endplate component 520 is generally concave. In the illustrated embodiment, two connector rods 570 connect the first endplate component 520 to the second endplate component 540. In some embodiments, the connector rods 570 are flexible. In the depicted example, the connector rods 570 each extend through the articulating element 560 from a first side of the spinal disc 510 to a second side of the spinal disc 510. In the illustrated embodiment, extending from the general central inner surface of the second endplate component 540 is a protruding platform 548 configured to connect to the articulating element 560 having an exterior articulating surface 562 and one or more outer apertures 566 configured to receive one or more connector rods 570. In some embodiments, the protruding platform 548 includes one or more inner apertures 550 configured to receive one or more connector rods 570. In some embodiments, the connector rods 570 connect the articulating element 560 to the protruding platform 548. In some embodiments, the connector rods 570 are inserted through outer apertures 566 and inner apertures 550 to fasten the articulating element 560 to the second endplate component 540. In some embodiments, the connector rods 570 are configured to pass through rod apertures 554, rod apertures 528, outer apertures 566, and inner apertures 550 to generally connect the first endplate 520 to the second endplate 540, as well as to connect both endplates 520 and 540 to the articulating element 560. In some embodiments, the articulating element 560 is formed of UHMWPE material. In the depicted example, the exterior articulating surface 562 of the articulating element 560 is substantially convex. In some embodiments, the exterior articulating surface 562 is substantially flat. In some embodiments, the apertures 550 and 566 are configured to allow one or more connector rods 570 to slightly move within the articulating element 560 while securing the articulating element 560 to the second endplate component 540. In some embodiments, the apertures 550 and 566, either alone or in combination, are configured to prevent the connector rods 570 from moving anterior-posterior or cephalad-caudal in relation to the second endplate component 540.

In some embodiments, the connector rods 570 are comprised of a flexible material such as NiTiNol wire, UHMWPE fibers, or similar material. In some embodiments, the connector rods 570 are held securely at each end within the rod apertures 528 in the first endplate component 520. In some embodiments, a middle portion of each connector rod 570 is retained within inner apertures 550 disposed on the articulating element 560. In some embodiments, the connector rods 570 are configured to connect the first endplate component 520 to the second endplate component 540, while also holding the articulating element 560 substantially in place. As shown in FIG. 28, in some embodiments, the second endplate component 540 includes one or more rod apertures 554. In some embodiments, the rod apertures 554 are configured to receive the rod connectors 570 and to fasten the rod connectors 570 to the second endplate component 540. In some embodiments, the flexibility of the connector rods 570 permits the first endplate component 520 to move and rotate with respect to the second endplate component 540, while substantially preventing over-rotation.

Figure 30:
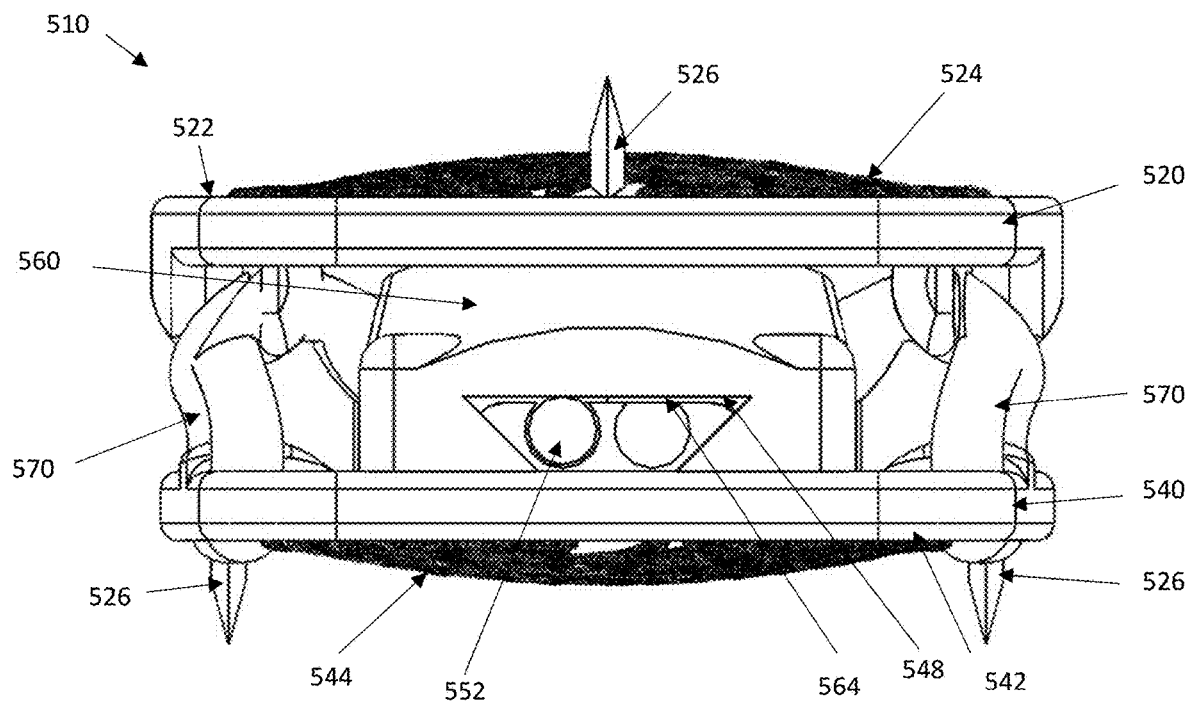
FIG. 30 is a cross sectional view of an interlocking prosthetic spinal disc in accordance with a sixth embodiment of the present invention.

FIG. 30 is a cross sectional view of an interlocking prosthetic spinal disc in accordance with a sixth embodiment of the present invention. In some embodiments, the articulating element 560 includes an endplate mating means configured to fasten the articulating element 560 to the second endplate component 540. In the illustrated embodiment, the endplate mating means is an indentation 564 in the articulating element 560 configured to mate with the protruding platform 548 on the second endplate component 540. In the depicted embodiments, the indentation 564 and the protruding platform 548 are configured in corresponding dovetail orientations which are adapted to secure the articulating element 560 to the second endplate component 540. In some embodiments, the second endplate component 540 is integrally formed with the articulating element 560. In the depicted example, the articulating element 560 has a generally rectangular frame and is disposed between the first endplate component 520 and the second endplate component 540. In some embodiments, the articulating element 560 includes an articulation surface 562 configured to rest or articulate against the articulating surface 534 of the first endplate component 520.

Figure 32:
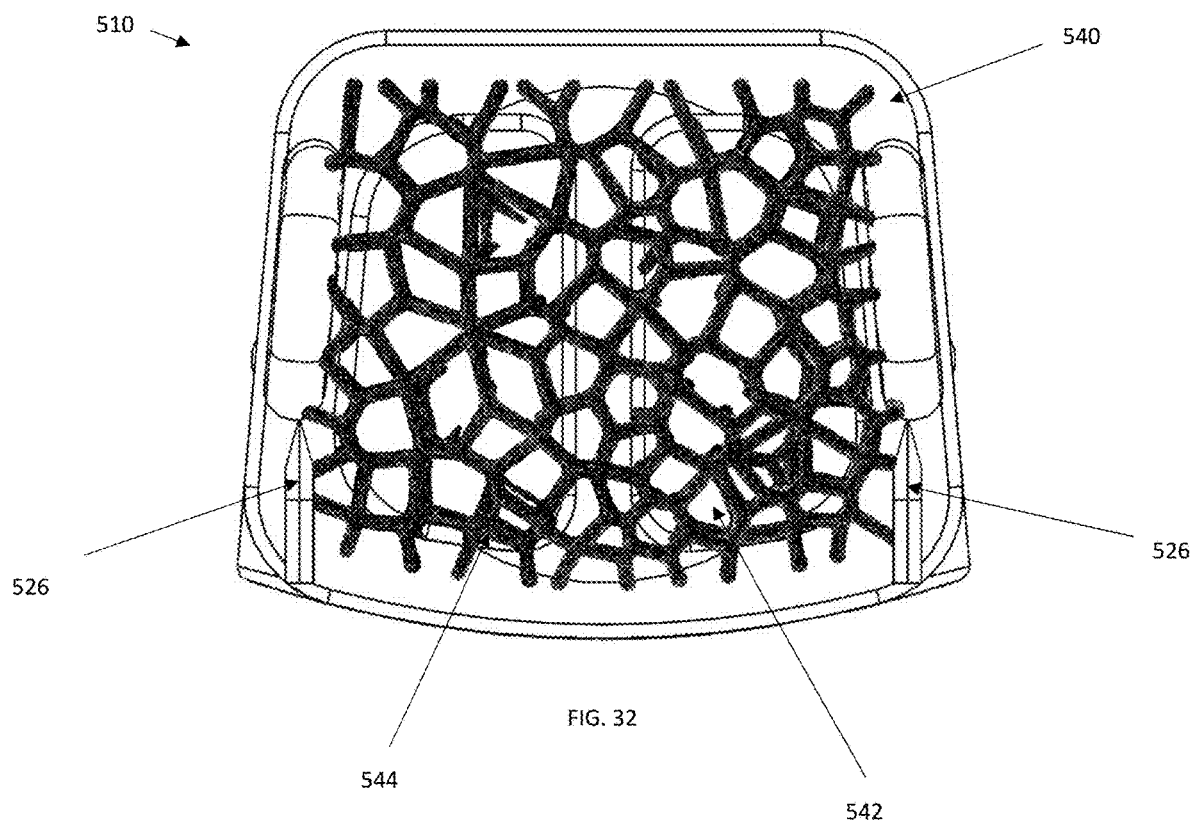
FIG. 32 is a bottom view of an interlocking prosthetic spinal disc in accordance with a sixth embodiment of the present invention.

FIG. 32 is a bottom view of an interlocking prosthetic spinal disc in accordance with a sixth embodiment of the present invention. In the depicted embodiment, the vertebral mating surface 542 of the second endplate component 540 includes a porous bone ingrowth surface 544 to promote bone mating and growth. In the illustrated embodiment, the second endplate component 540 includes two keels 526.

In some scenarios, a spinal disc may be displaced or damaged due to trauma, disease, degenerative defects, or wear over an extended period of time, causing, in some instances, disabling back pain. In some situations, herniated or "slipped" nucleus tissue may apply pressure to spinal nerves, resulting in leg pain, loss of muscle control, or even paralysis. Alternatively, with discal degeneration, the nucleus may lose its water binding ability and deflate, wherein the height of the nucleus decreases, causing the annulus to buckle in areas where laminated plies are loosely bonded. As these overlapping laminated plies of the annulus begin to buckle and separate, either circumferential or radial annular tears may occur, which may contribute to persistent or disabling back pain. Adjacent, ancillary spinal facet joints will also be forced into an overriding position, which may create additional back pain.

Various prior art approaches illustrative of previous attempts to imitate the functions of a normal spinal disc with a disc prosthesis have been developed. The first prosthetics embodied a wide variety of ideas, such as ball bearings, springs, metal spikes and other perceived aids. These prosthetics are all made to replace all or most of the intervertebral disc tissue and are large and rigid. Many of the current designs for prosthetic discs are large, inflexible and provide minimal articulation. Moreover, many of these prosthetic disc devices fail to incorporate a resistance measure to prevent over-extension or rotation of the device.

In various embodiments of the present invention, an embodiment prosthetic spinal implant is configured to provide the same articulation as a healthy intervertebral disc. In some examples, the prosthetic spinal disc is configured to replace a damaged disc between two vertebrae of a spine. In some embodiments, the prosthetic spinal implant includes interlocking components which are configured to articulate against one another in order to restore motion to the affected disc space while limiting or altogether preventing the over extension and over rotation of the affected disc space.

The prosthetic spinal implant of the present invention includes articulating surfaces, configured to permit the motion of the first and second endplate components relative to one another. In some embodiments, the interior or exterior surfaces of the first and second endplate elements may include an articulating surface. In some embodiments, the interior surface of the first and second endplate components or bases include an articulating surface. In an exemplary embodiment, the articulation function of the prosthetic disc is configured to allow the disc to rotate axially and radially and allow for flexion, extension and bending of the spine. In some embodiments, the articulation function of the prosthetic disc may be configured to permit movement in one, two, or more than two directions.

In the Summary above and in this Detailed Description, and the Claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments, elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of." In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number) (a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f).

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

The invention claimed is:

1. A prosthetic spinal implant apparatus configured to articulate in at least two planes, comprising:
   a first endplate and a second endplate forming an articulating joint, wherein each endplate has a base with an exterior surface adapted to engage with bone;
   an articulating element attached to an interior surface of the second endplate; and
   one or more connector rods extending entirely through the articulating element to connect the first endplate to the second endplate, wherein each of the endplates is formed with apertures configured to receive the connector rods and the connector rods extend through the articulating element from a first lateral side of the prosthetic spinal implant to a second lateral side of the prosthetic spinal implant to connect the first endplate to the second endplate and each of the endplates to the articulating element.

2. The apparatus of claim 1, wherein the articulating element attaches to a protruding platform formed on the interior surface of the second endplate.

3. The apparatus of claim 2, wherein an indentation formed in the articulating element mates with the protruding platform in a dovetail configuration.

4. The apparatus of claim 1, wherein the articulating element is integrally formed on the interior surface of the second endplate.

5. The apparatus of claim 1, wherein the exterior surface includes one or more sharpened protrusions.

6. The apparatus of claim 5, wherein the sharpened protrusions are keels.

7. The apparatus of claim 1, wherein the exterior surface includes a bony ingrowth region.

8. The apparatus of claim 7, wherein the bony ingrowth region comprises an osteoconductive material.

9. The apparatus of claim 1, wherein one or more inserter apertures configured to receive an inserter tool are disposed on at least one of the pair of bases.

10. The apparatus of claim 1, wherein the connector rods are formed of ultra-high-molecular-weight polyethylene.

11. The apparatus of claim 1, wherein at least a portion of each the endplates is formed of ultra-high-molecular-weight polyethylene.

12. The apparatus of claim 1, wherein an interior surface of the first endplate and an exterior surface the articulating element are each configured with an articulation surface and the articulation surface of the first endplate is configured to articulate against the articulation surface of the articulating element.

13. The apparatus of claim 1, wherein the connector rods prevent over-rotation of the first endplate relative to the second endplate.

14. The apparatus of claim 12, wherein the articulation surface of the first endplate is concave and the articulation surface of the articulating element is convex.

15. The apparatus of claim 12, wherein the articulation surface of the articulating element is flat.

16. A prosthetic spinal implant apparatus configured to articulate in at least two planes, comprising:
   a first endplate and a second endplate forming an articulating joint, wherein each endplate has a base with an exterior surface adapted to engage with bone;
   an articulating element attached to an interior surface of the second endplate;
   an articulation surface configured on each of an interior surface of the first endplate and an exterior surface the articulating element, wherein the articulation surface of the first endplate is configured to articulate against the articulation surface of the articulating element and the articulation surface of the articulating element is flat; and
   one or more connector rods extending through the articulating element to connect the first endplate to the second endplate.

17. A prosthetic spinal implant apparatus configured to articulate in at least two planes, comprising:
   a first endplate and a second endplate forming an articulating joint, wherein each endplate has a base with an exterior surface adapted to engage with bone;
   an articulating element positioned between the first endplate and the second endplate; and
   one or more flexible connector rods extending through the articulating element to connect the first endplate to the second endplate, wherein the connector rods extend through the articulating element from a first lateral side of the prosthetic spinal implant to a second lateral side of the prosthetic spinal implant thereby connecting the first endplate to the second endplate and holding the articulating element in place between the endplates.

* * * * *